United States Patent
Kim et al.

(10) Patent No.: US 9,868,751 B2
(45) Date of Patent: Jan. 16, 2018

(54) PHOSPHONIUM COMPOUND, EPOXY RESIN COMPOSITION INCLUDING THE SAME AND SEMICONDUCTOR DEVICE PREPARED FROM THE SAME

(71) Applicant: SAMSUNG SDI CO., LTD., Yongin-si, Gyeonggi-do (KR)

(72) Inventors: Min Gyum Kim, Uiwang-si (KR); Ki Hyeok Kwon, Uiwang-si (KR); Dong Hwan Lee, Uiwang-si (KR); Joo Young Chung, Uiwang-si (KR); Jin Min Cheon, Uiwang-si (KR); Jin Woo Choi, Uiwang-si (KR)

(73) Assignee: SAMSUNG SDI CO., LTD., Yongin-Si, Gyeonggi-Do (KR)

( * ) Notice: Subject to any disclaimer, the term of this patent is extended or adjusted under 35 U.S.C. 154(b) by 52 days.

(21) Appl. No.: 14/918,916

(22) Filed: Oct. 21, 2015

(65) Prior Publication Data
US 2016/0115184 A1   Apr. 28, 2016

(30) Foreign Application Priority Data

Oct. 22, 2014 (KR) .......................... 10-2014-0143638
Apr. 24, 2015 (KR) .......................... 10-2015-0058072

(51) Int. Cl.
*C07F 9/54* (2006.01)
*C08L 63/00* (2006.01)
(Continued)

(52) U.S. Cl.
CPC .............. *C07F 9/5442* (2013.01); *C07C 39/08* (2013.01); *C07C 39/12* (2013.01); *C07C 39/17* (2013.01);
(Continued)

(58) Field of Classification Search
CPC ........ C08G 59/688; C07F 9/54–9/5463; C08L 63/00–63/10; C09D 163/00–163/10;
(Continued)

(56) References Cited

U.S. PATENT DOCUMENTS 7,723,444 B2 * 5/2010 Akiyama ............. C08G 59/621
257/793
2004/0039154 A1 * 2/2004 Okubo ................. C07F 9/5442
528/408
(Continued)

FOREIGN PATENT DOCUMENTS

CN        101107285 A     1/2008
CN        103896983 A     7/2014
(Continued)

OTHER PUBLICATIONS
Machine translation of JP 2002-105171 A.*
(Continued)

*Primary Examiner* — Kregg T Brooks
(74) *Attorney, Agent, or Firm* — Lee & Morse, P.C.

(57) ABSTRACT

A phosphonium compound, an epoxy resin composition, a method of preparing a phosphonium compound, and a semiconductor device encapsulated with the epoxy resin composition, the compound being represented by Formula 1:

[Formula 1]

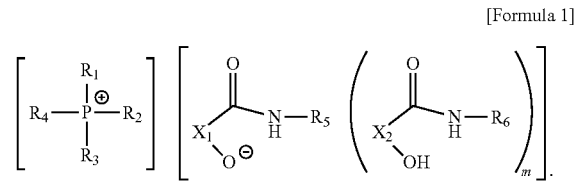

21 Claims, 1 Drawing Sheet

(51) Int. Cl.

| | |
|---|---|
| *H01L 23/29* | (2006.01) |
| *H01L 23/31* | (2006.01) |
| *C08K 5/50* | (2006.01) |
| *C07C 233/65* | (2006.01) |
| *C07C 233/75* | (2006.01) |
| *C07C 235/66* | (2006.01) |
| *C07C 323/20* | (2006.01) |
| *C07C 39/08* | (2006.01) |
| *C07C 39/17* | (2006.01) |
| *C07C 49/83* | (2006.01) |
| *C08G 59/68* | (2006.01) |
| *C09D 163/00* | (2006.01) |
| *C08K 5/49* | (2006.01) |
| *H01L 23/00* | (2006.01) |
| *C07C 259/10* | (2006.01) |
| *C07C 235/64* | (2006.01) |
| *C07C 39/12* | (2006.01) |
| *C08G 59/62* | (2006.01) |

(52) U.S. Cl.
 CPC .......... *C07C 233/65* (2013.01); *C07C 235/64* (2013.01); *C07C 235/66* (2013.01); *C07C 259/10* (2013.01); *C07C 323/20* (2013.01); *C08G 59/621* (2013.01); *C08G 59/688* (2013.01); *C08K 5/49* (2013.01); *C08K 5/50* (2013.01); *C09D 163/00* (2013.01); *H01L 23/295* (2013.01); *H01L 24/29* (2013.01); *C07C 2603/18* (2017.05); *H01L 23/3121* (2013.01); *H01L 24/13* (2013.01); *H01L 24/16* (2013.01); *H01L 24/32* (2013.01); *H01L 24/81* (2013.01); *H01L 24/92* (2013.01); *H01L 2224/131* (2013.01); *H01L 2224/16225* (2013.01); *H01L 2224/16227* (2013.01); *H01L 2224/2929* (2013.01); *H01L 2224/29298* (2013.01); *H01L 2224/32225* (2013.01); *H01L 2224/73204* (2013.01); *H01L 2224/81192* (2013.01); *H01L 2224/92125* (2013.01); *H01L 2924/14* (2013.01); *H01L 2924/181* (2013.01)

(58) Field of Classification Search
 CPC ........ C09J 163/00–163/10; C08K 5/49; C08K 5/50; C07C 233/64; C07C 233/65; C07C 233/66; C07C 233/75; C07C 259/10; C07C 323/20; C07C 39/08; C07C 39/12; C07C 39/17; H01L 23/293; H01L 23/295
 See application file for complete search history.

(56) References Cited

U.S. PATENT DOCUMENTS

| | | | |
|---|---|---|---|
| 2007/0149776 A1* | 6/2007 | Lindenschmidt | A61K 31/33 540/200 |
| 2010/0148379 A1 | 6/2010 | Noro et al. | |
| 2012/0046244 A1 | 2/2012 | Rogers et al. | |
| 2013/0062748 A1* | 3/2013 | Tabei | H01L 23/293 257/676 |
| 2014/0179827 A1 | 6/2014 | Kim et al. | |
| 2016/0368937 A1* | 12/2016 | Lee | C07F 9/5442 |
| 2016/0379909 A1* | 12/2016 | Cheon | C09D 163/00 523/447 |
| 2017/0002192 A1* | 1/2017 | Chung | C08L 63/00 |

FOREIGN PATENT DOCUMENTS

| | | | |
|---|---|---|---|
| JP | 2002-105171 A | | 4/2002 |
| JP | 2002105171 A | * | 4/2002 |
| JP | 2006-307131 A | | 11/2006 |
| JP | 4569076 | | 8/2010 |
| KR | 10-2014-0082528 A | | 7/2014 |

OTHER PUBLICATIONS

Taiwanese Office Action dated May 4, 2016 in Corresponding Taiwanese Patent Application No. 104134608.
Provisional double patenting rejection over claims of the above-identified application; USPTO Office action dated Mar. 9, 2017, in U.S. Appl. No. 15/188,454.
Provisional double patenting rejection over claims of the above-identified application; USPTO Office action dated Mar. 14, 2017, in U.S. Appl. No. 15/200,009.
Office Action dated Feb. 4, 2017 in the corresponding Chinese Patent Application No. 201510695432.3.
Office Action dated Nov. 29, 2016 in the corresponding Korean Patent Application No. 2014-0143638.

* cited by examiner

PHOSPHONIUM COMPOUND, EPOXY RESIN COMPOSITION INCLUDING THE SAME AND SEMICONDUCTOR DEVICE PREPARED FROM THE SAME

CROSS-REFERENCE TO RELATED APPLICATION

Korean Patent Application Nos. 10-2014-0143638, filed on Oct. 22, 2014, and 10-2015-0058072, filed on Apr. 24, 2015, in the Korean Intellectual Property Office, and entitled: "Phosphonium Compound, Epoxy Resin Composition Comprising the Same and Semiconductor Device Prepared From the Same," are incorporated by reference herein in its entirety.

1. Field

Embodiments relate to a phosphonium compound, an epoxy resin composition including the same, and a semiconductor device prepared from the same.

2. Description of the Related Art

Transfer molding is widely used as a method of packaging semiconductor devices, such as ICs (Integrated Circuits) and LSI chips, with epoxy resin compositions to obtain semiconductor devices due to its advantages of low cost and suitability for mass production.

Summary

Embodiments are directed to a phosphonium compound, an epoxy resin composition including the same, and a semiconductor device prepared from the same.

The embodiments may be realized by providing a phosphonium compound represented by Formula 1:

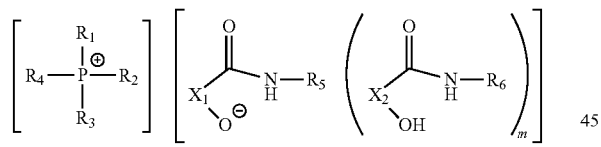

[Formula 1]

wherein, in Formula 1, $R_1$, $R_2$, $R_3$, and $R_4$ are each independently a substituted or unsubstituted $C_1$ to $C_{30}$ aliphatic hydrocarbon group, a substituted or unsubstituted $C_6$ to $C_{30}$ aromatic hydrocarbon group, or a substituted or unsubstituted $C_1$ to $C_{30}$ hydrocarbon group including a heteroatom; $X_1$ and $X_2$ are each independently a substituted or unsubstituted $C_6$ to $C_{30}$ arylene group, a substituted or unsubstituted $C_3$ to $C_{10}$ cycloalkylene group, or a substituted or unsubstituted $C_1$ to $C_{20}$ alkylene group; $R_5$ and $R_6$ are each independently hydrogen, a hydroxyl group, a substituted or unsubstituted $C_1$ to $C_{20}$ alkyl group, a substituted or unsubstituted $C_6$ to $C_{30}$ aryl group, a substituted or unsubstituted $C_3$ to $C_{30}$ heteroaryl group, a substituted or unsubstituted $C_3$ to $C_{10}$ cycloalkyl group, a substituted or unsubstituted $C_3$ to $C_{10}$ heterocycloalkyl group, a substituted or unsubstituted $C_7$ to $C_{30}$ arylalkyl group, or a substituted or unsubstituted $C_1$ to $C_{30}$ heteroalkyl group; and m is an integer of 0 to 5.

$R_1$, $R_2$, $R_3$, and $R_4$ may each independently be a substituted or unsubstituted $C_6$ to $C_{30}$ aryl group.

At least one of $R_1$, $R_2$, $R_3$, and $R_4$ may be substituted with a hydroxyl group.

The phosphonium compound represented by Formula 1 may be a compound represented by one of the following Formulae 1a to 1o:

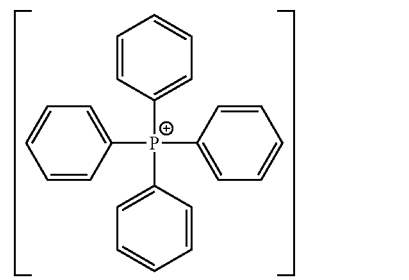

[Formula 1a]

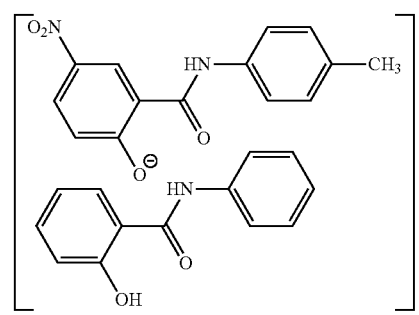

[Formula 1b]

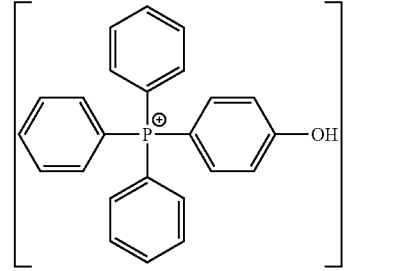

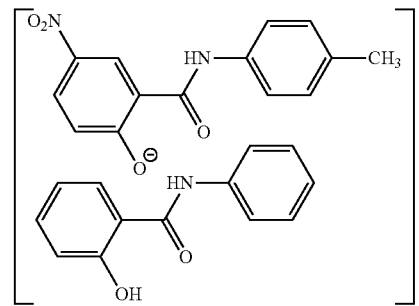

[Formula 1b]

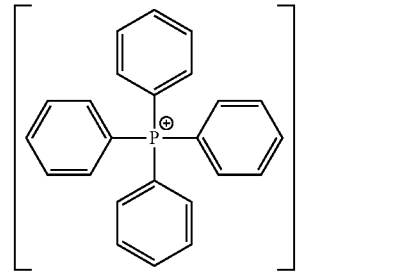

[Formula 1c]

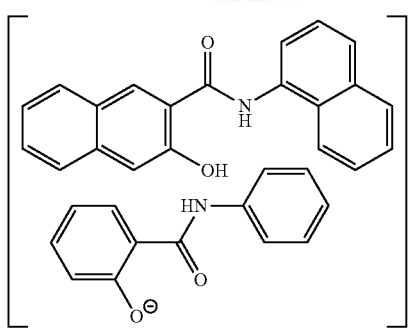
[Formula 1d]
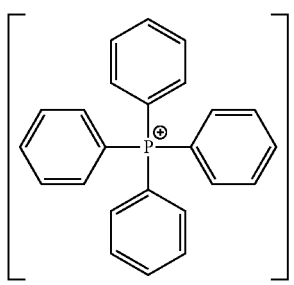
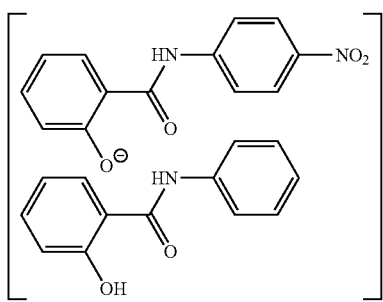
[Formula 1e]
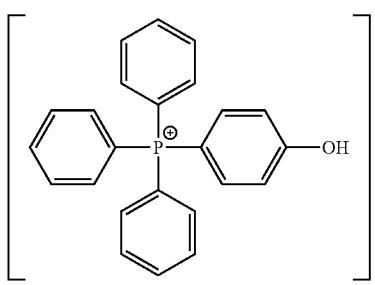
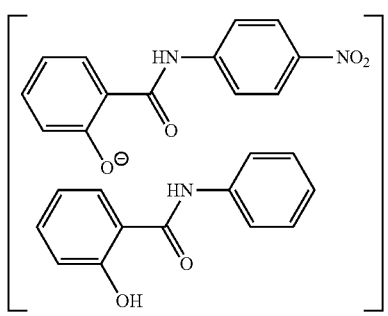
[Formula 1f]
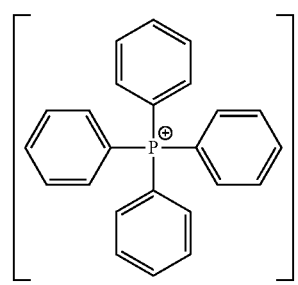
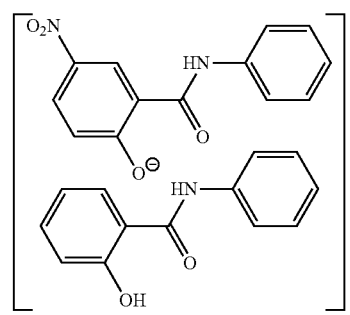
[Formula 1g]
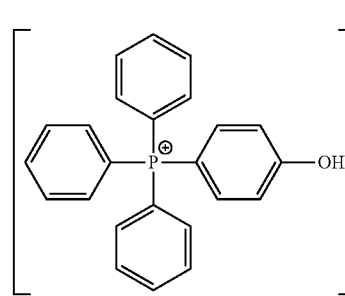
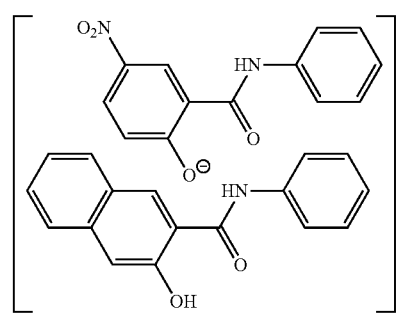
[Formula 1h]
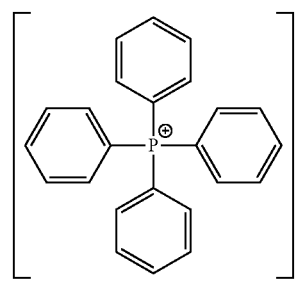
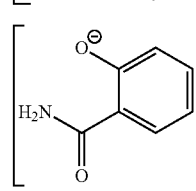

[Formula 1i]
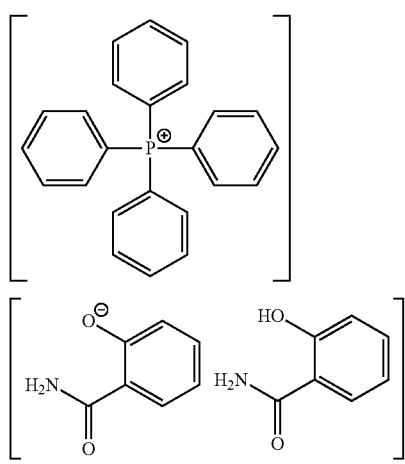
[Formula 1j]
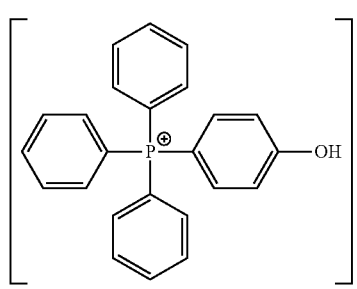
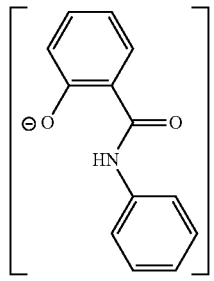
[Formula 1k]
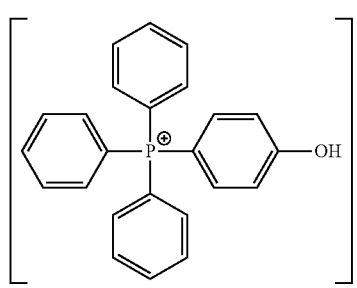
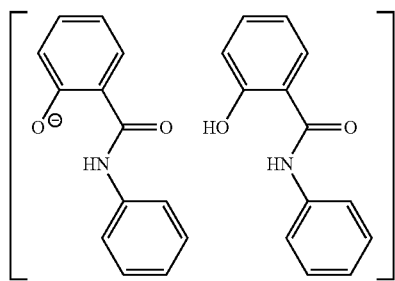
[Formula 1l]
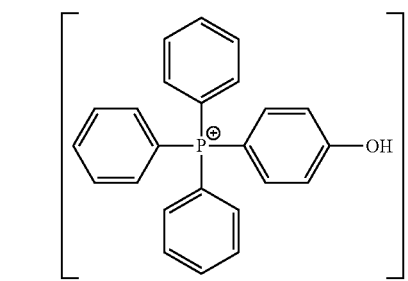
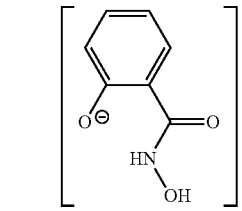
[Formula 1m]
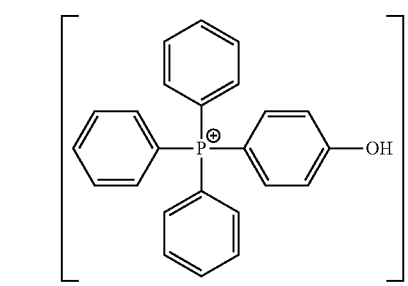
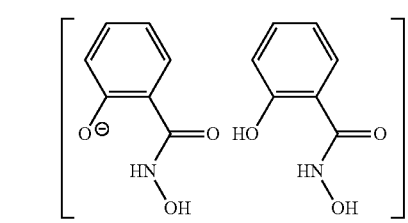
[Formula 1n]
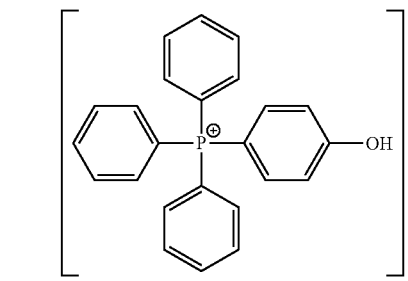
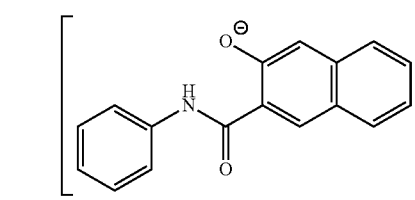

[Formula 1o]

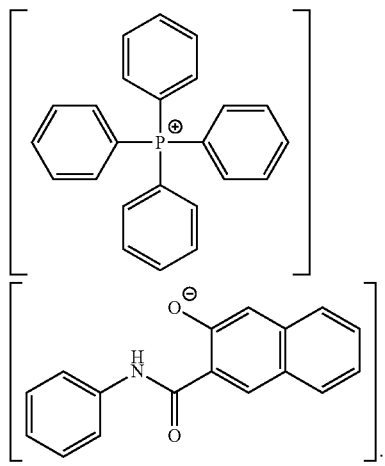

The embodiments may be realized by providing a phosphonium compound represented by Formula 2:

[Formula 2]

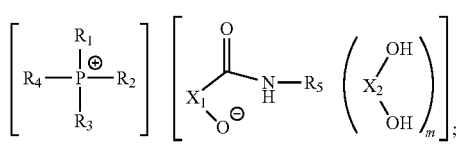

wherein, in Formula 2, $R_1$, $R_2$, $R_3$, and $R_4$ are each independently a substituted or unsubstituted $C_1$ to $C_{30}$ aliphatic hydrocarbon group, a substituted or unsubstituted $C_6$ to $C_{30}$ aromatic hydrocarbon group, or a substituted or unsubstituted $C_1$ to $C_{30}$ hydrocarbon group including a heteroatom; $X_1$ and $X_2$ are each independently a substituted or unsubstituted $C_6$ to $C_{30}$ arylene group, a substituted or unsubstituted $C_3$ to $C_{10}$ cycloalkylene group, or a substituted or unsubstituted $C_1$ to $C_{20}$ alkylene group; $R_5$ is hydrogen, a hydroxyl group, a substituted or unsubstituted $C_1$ to $C_{20}$ alkyl group, a substituted or unsubstituted $C_6$ to $C_{30}$ aryl group, a substituted or unsubstituted $C_3$ to $C_{30}$ heteroaryl group, a substituted or unsubstituted $C_3$ to $C_{10}$ cycloalkyl group, a substituted or unsubstituted $C_3$ to $C_{10}$ heterocycloalkyl group, a substituted or unsubstituted $C_7$ to $C_{30}$ arylalkyl group, or a substituted or unsubstituted $C_1$ to $C_{30}$ heteroalkyl group; and m is 1 or 2.

$R_1$, $R_2$, $R_3$, and $R_4$ may each independently be a substituted or unsubstituted $C_6$ to $C_{30}$ aryl group.

At least one of $R_1$, $R_2$, $R_3$, and $R_4$ may be substituted with a hydroxyl group.

The phosphonium compound represented by Formula 2 may be a compound represented by one of the following Formulae 2a to 2j:

[Formula 2a]

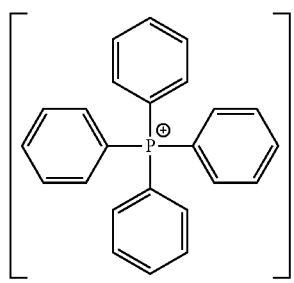

[Formula 2b]

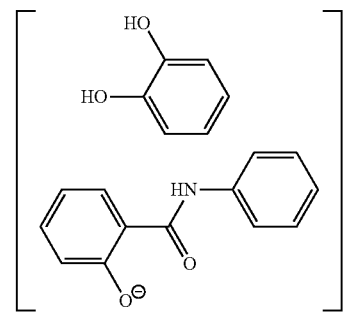
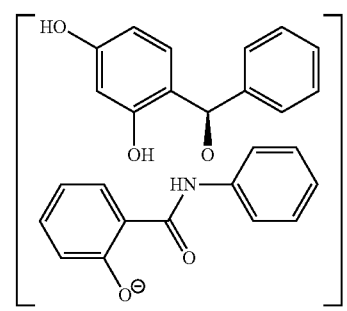

[Formula 2c]

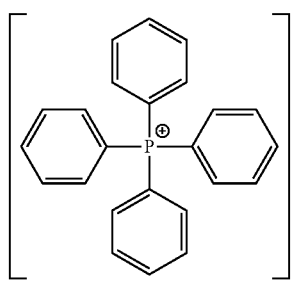
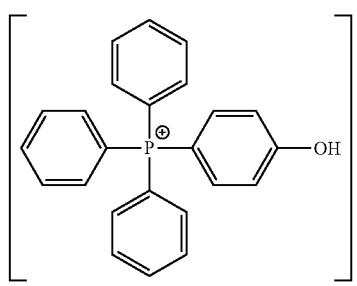
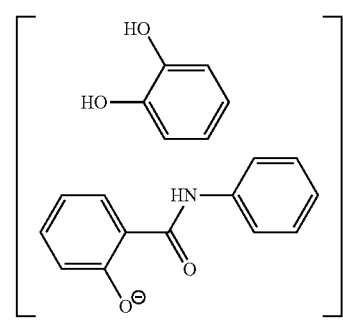

[Formula 2d]
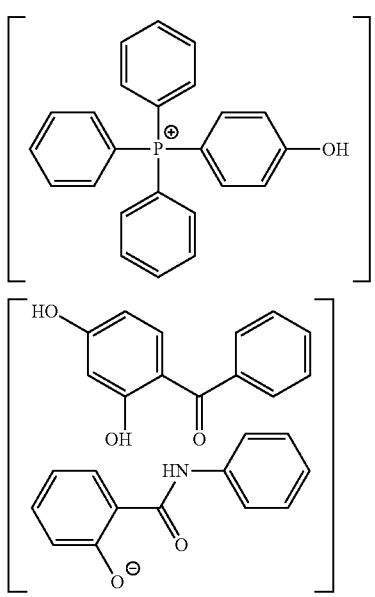
[Formula 2e]
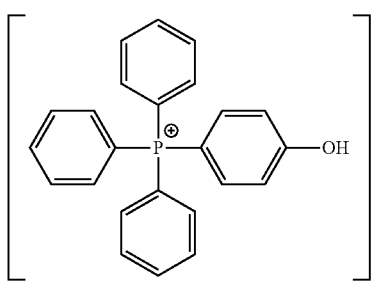
[Formula 2f]
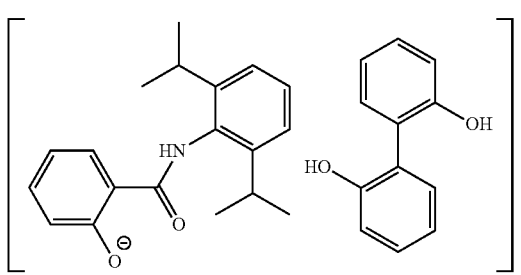
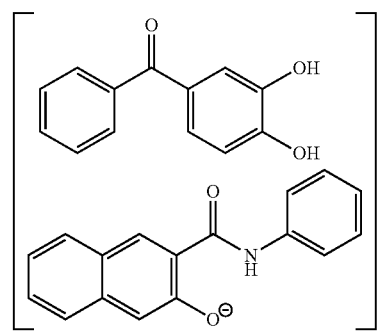
[Formula 2g]
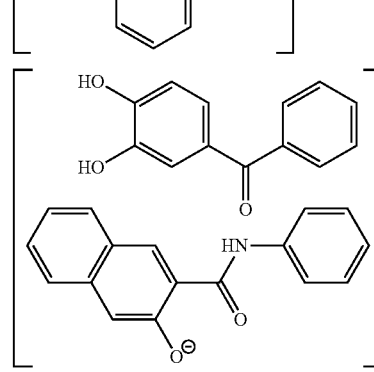
[Formula 2h]
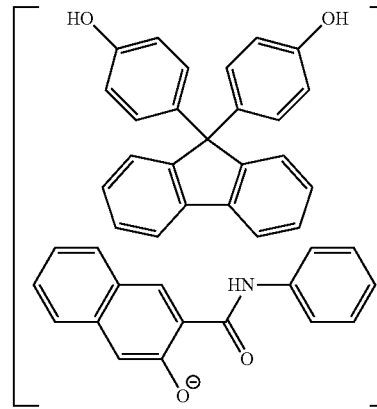

-continued

[Formula 2i]

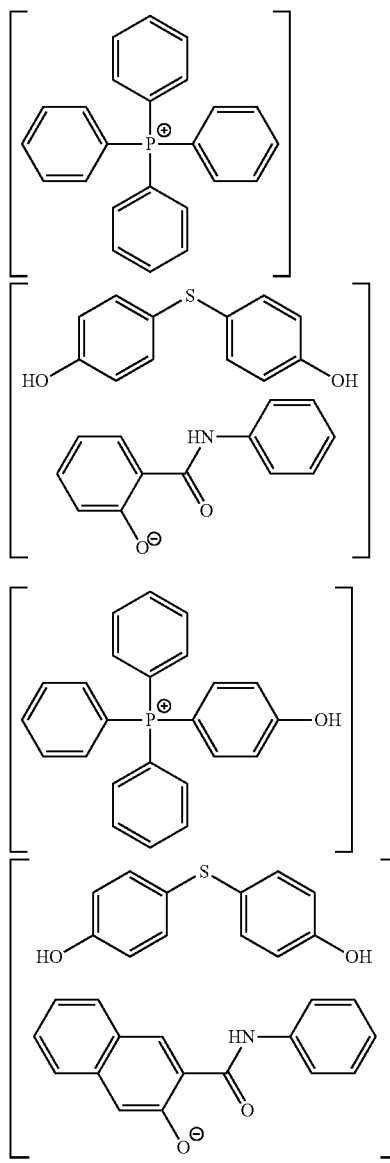

[Formula 2j]

The embodiments may be realized by providing a method of preparing a phosphonium compound, the method comprising reacting a phosphonium cation-containing compound represented by Formula 3 with an anilide anion-containing compound represented by Formula 4.

[Formula 3]

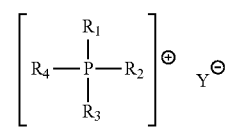

wherein, in Formula 3, $R_1$, $R_2$, $R_3$, and $R_4$ are each independently a substituted or unsubstituted $C_1$ to $C_{30}$ aliphatic hydrocarbon group, a substituted or unsubstituted $C_6$ to $C_{30}$ aromatic hydrocarbon group, or a substituted or unsubstituted $C_1$ to $C_{30}$ hydrocarbon group including a heteroatom; and Y is a halogen,

[Formula 4]

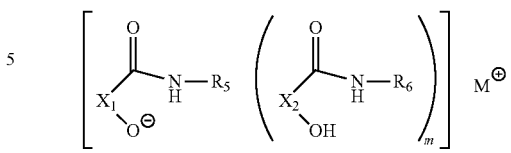

wherein, in Formula 4, $X_1$ and $X_2$ are each independently a substituted or unsubstituted $C_6$ to $C_{30}$ arylene group, a substituted or unsubstituted $C_3$ to $C_{10}$ cycloalkylene group, or a substituted or unsubstituted $C_1$ to $C_{20}$ alkylene group; $R_5$ and $R_6$ are each independently hydrogen, a hydroxyl group, a substituted or unsubstituted $C_1$ to $C_{20}$ alkyl group, a substituted or unsubstituted $C_6$ to $C_{30}$ aryl group, a substituted or unsubstituted $C_3$ to $C_{30}$ heteroaryl group, a substituted or unsubstituted $C_3$ to $C_{10}$ cycloalkyl group, a substituted or unsubstituted $C_3$ to $C_{10}$ heterocycloalkyl group, a substituted or unsubstituted $C_7$ to $C_{30}$ arylalkyl group, or a substituted or unsubstituted $C_1$ to $C_{30}$ heteroalkyl group; m is an integer of 0 to 5; and M is an alkali metal or silver.

The embodiments may be realized by providing a method of preparing a phosphonium compound, the method comprising reacting a phosphonium cation-containing compound represented by Formula 3 with an anilide anion-containing compound represented by Formula 5.

[Formula 3]

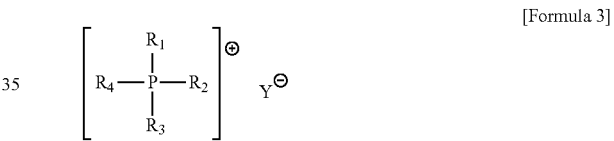

wherein, in Formula 3, $R_1$, $R_2$, $R_3$, and $R_4$ are each independently a substituted or unsubstituted $C_1$ to $C_{30}$ aliphatic hydrocarbon group, a substituted or unsubstituted $C_6$ to $C_{30}$ aromatic hydrocarbon group, or a substituted or unsubstituted $C_1$ to $C_{30}$ hydrocarbon group including a hetero atom; and Y is a halogen,

[Formula 5]

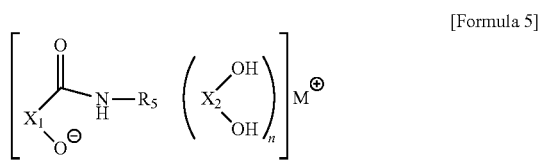

wherein, in Formula 5, $X_1$ and $X_2$ are each independently a substituted or unsubstituted $C_6$ to $C_{30}$ arylene group, a substituted or unsubstituted $C_3$ to $C_{10}$ cycloalkylene group, or a substituted or unsubstituted $C_1$ to $C_{20}$ alkylene group; $R_5$ is hydrogen, a hydroxyl group, a substituted or unsubstituted $C_1$ to $C_{20}$ alkyl group, a substituted or unsubstituted $C_6$ to $C_{30}$ aryl group, a substituted or unsubstituted $C_3$ to $C_{30}$ heteroaryl group, a substituted or unsubstituted $C_3$ to $C_{10}$ cycloalkyl group, a substituted or unsubstituted $C_3$ to $C_{10}$ heterocycloalkyl group, a substituted or unsubstituted $C_7$ to $C_{30}$ arylalkyl group, or a substituted or unsubstituted $C_1$ to $C_{30}$ heteroalkyl group; n is 1 or 2; and M is an alkali metal or silver.

The embodiments may be realized by providing an epoxy resin composition including an epoxy resin, a curing agent, inorganic filler, and a curing catalyst, wherein the curing catalyst includes the phosphonium compound according to an embodiment.

The epoxy resin may include at least one of bisphenol A type epoxy resin, bisphenol F type epoxy resin, phenol novolac epoxy resin, tert-butyl catechol epoxy resin, naphthalene epoxy resin, glycidyl amine epoxy resin, cresol novolac epoxy resin, biphenyl epoxy resin, linear aliphatic epoxy resin, cycloaliphatic epoxy resin, heterocyclic epoxy resin, spiro ring-containing epoxy resin, cyclohexane dimethanol type epoxy resin, trimethylol type epoxy resin, and halogenated epoxy resin.

The curing agent may include a phenol resin.

The curing agent may include at least one of phenolaralkyl phenol resin, phenol novolac phenol resin, xyloc phenol resin, cresol novolac phenol resin, naphthol phenol resin, terpene phenol resin, multifunctional phenol resin, dicyclopentadiene-based phenol resin, novolac phenol resin synthesized from bisphenol A and resol, a polyhydric phenol compound, an acid anhydride, and an aromatic amine.

The curing catalyst may be present in the composition in an amount of 0.01 wt % to 5 wt %, based on a total weight of the epoxy resin composition.

The phosphonium compound may be present in the curing catalyst in an amount of 10 wt % to 100 wt %, based on a total weight of the curing catalyst.

The epoxy resin composition may have storage stability of 80% or more, as calculated by the Equation 2:

Storage stability=$(F1-F0)/F0 \times 100$, wherein F1 is a flow length in inches of the epoxy resin composition measured after storing the composition at 25° C./50% RH for 72 hours using a transfer molding press at 175° C. and 70 kgf/cm² in accordance with EMMI-1-66, and F0 is an initial flow length in inches of the epoxy resin composition.

The epoxy resin composition may have a curing shrinkage rate of less than 0.4%, as calculated by the Equation 1:

Curing shrinkage=$|C-D|/C \times 100$, wherein C is a length of a specimen obtained by subjecting an epoxy resin composition to a transfer molding at 175° C. under a load of 70 kgf/cm², and D is a length of the specimen after post-curing the specimen at 170° C. to 180° C. for 4 hours and cooling.

The embodiments may be realized by providing a semiconductor device encapsulated with the epoxy resin composition according to an embodiment.

BRIEF DESCRIPTION OF THE DRAWINGS

Features will be apparent to those of skill in the art by describing in detail exemplary embodiments with reference to the attached drawings in which.

DETAILED DESCRIPTION

Figure 1:
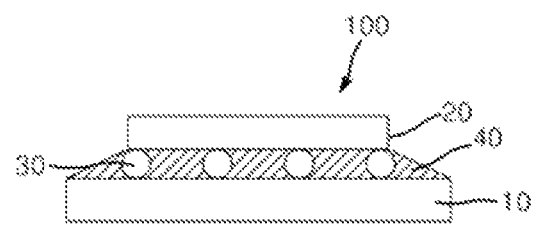
FIG. 1 illustrates a cross sectional view of a semiconductor device according to one embodiment.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing figures, the dimensions of layers and regions may be exaggerated for clarity of illustration. It will also be understood that when a layer or element is referred to as being "on" another layer or element, it can be directly on the other layer or element, or intervening layers may also be present. Like reference numerals refer to like elements throughout.

As used herein, the term "substituted" in "substituted or unsubstituted" means that at least one hydrogen atom in the corresponding groups is substituted with a hydroxyl group, a halogen atom, an amino group, a nitro group, a cyano group, a $C_1$ to $C_{20}$ alkyl group, a $C_1$ to $C_{20}$ haloalkyl group, a $C_6$ to $C_{20}$ aryl group, a $C_3$ to $C_{30}$ heteroaryl group, a $C_3$ to $C_{10}$ cycloalkyl group, a $C_3$ to $C_{10}$ heterocycloalkyl group, a $C_7$ to $C_{30}$ arylalkyl group, or a $C_1$ to $C_{30}$ heteroalkyl group. The term "halo" means fluorine, chlorine, iodine, or bromine.

As used herein, the term "aryl group" refers to a substituent in which all elements in the cyclic substituent have p-orbitals and the p-orbitals form a conjugated system. Aryl groups include mono- or fused functional groups (namely, rings of carbon atoms which share adjacent electron pairs). The term "unsubstituted aryl group" refers to a monocyclic or fused polycyclic $C_6$ to $C_{30}$ aryl group. Examples of unsubstituted aryl groups include phenyl groups, biphenyl groups, naphthyl groups, naphthol groups, and anthracenyl groups, without being limited thereto.

As used herein, the term "heteroaryl group" means a $C_6$ to $C_{30}$ aryl group in which a ring comprises carbon atoms and 1 to 3 heteroatoms selected from nitrogen, oxygen, sulfur and phosphorus. Examples of heteroaryl groups include, but are not limited to, pyridinyl, pyrazinyl, pyrimidyl, pyridazinyl, triazinyl, quinolinyl, isoquinolinyl, quinoxalinyl, acridinyl, quinazolinyl, cinnolinyl, phthalazinyl, thiazolyl, benzothiazolyl, isoxazolyl, benzisoxazolyl, oxazolyl, benzoxazolyl, pyrazolyl, indazolyl, imidazolyl, benzimidazolyl, purinyl, thiophenyl, benzothiophenyl, furanyl, benzofuranyl, and isobenzofuranyl.

As used herein, the term "hetero" in "heterocycloalkyl group", "heteroaryl group", "heterocycloalkylene group", and "heteroaryllene group" refers to an atom selected from nitrogen, oxygen, sulfur, or phosphorus.

The phosphonium compound according to an embodiment may include, e.g., a phosphonium cation and an anion having a hydroxyl group and an amide group at the same time. In an implementation, the phosphonium compound may be represented by Formula 1.

[Formula 1]

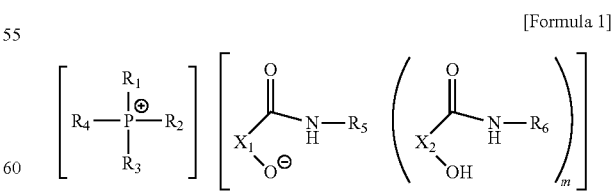

In Formula 1, $R_1$, $R_2$, $R_3$, and $R_4$ may each independently be or include, e.g., a substituted or unsubstituted $C_1$ to $C_{30}$ aliphatic hydrocarbon group, a substituted or unsubstituted $C_6$ to $C_{30}$ aromatic hydrocarbon group, or a substituted or unsubstituted $C_1$ to $C_{30}$ hydrocarbon group including a hetero atom. $X_1$ and $X_2$ may each independently be or include, e.g., a substituted or unsubstituted $C_6$ to $C_{30}$ arylene group, a substituted or unsubstituted $C_3$ to $C_{10}$ cycloalkylene group, or a substituted or unsubstituted $C_1$ to $C_{20}$ alkylene group. $R_5$ and $R_6$ may each independently be or include, e.g., hydrogen, a hydroxyl group, a substituted or unsubstituted $C_1$ to $C_{20}$ alkyl group, a substituted or unsubstituted $C_6$ to $C_{30}$ aryl group, a substituted or unsubstituted $C_3$ to $C_{30}$ heteroaryl group, a substituted or unsubstituted $C_3$ to $C_{10}$ cycloalkyl group, a substituted or unsubstituted $C_3$ to $C_{10}$ heterocycloalkyl group, a substituted or unsubstituted $C_7$ to $C_{30}$ arylalkyl group, or a $C_1$ to $C_{30}$ heteroalkyl group. m may be, e.g., an integer of 0 to 5.

In Formula 1, $R_1$, $R_2$, $R_3$, and $R_4$ may each independently be or include, e.g., a substituted or unsubstituted $C_6$ to $C_{30}$ aryl group.

In an implementation, in Formula 1, at least one of $R_1$, $R_2$, $R_3$, and $R_4$ may be substituted with a hydroxyl group.

In an implementation, the phosphonium compound represented by Formula 1 may be represented by one of the following Formulae 1a to 1o:

[Formula 1a]

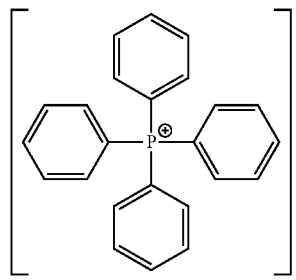

[Formula 1b]

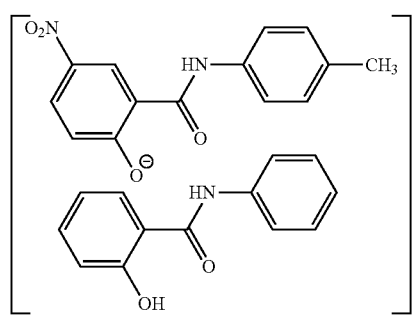

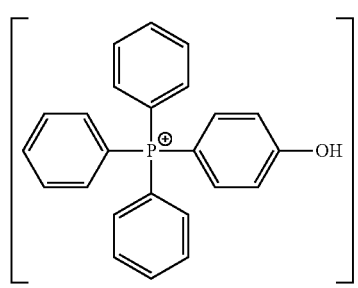

[Formula 1c]

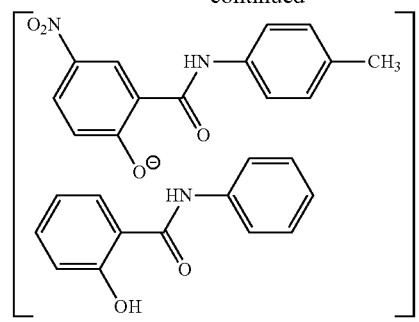

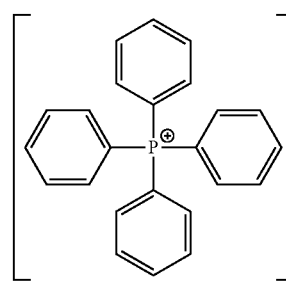

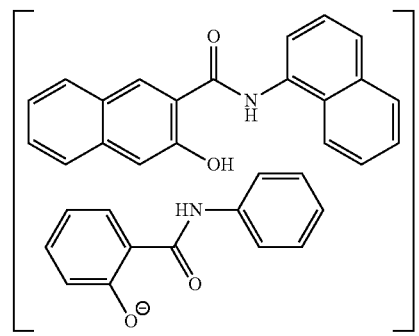

[Formula 1d]

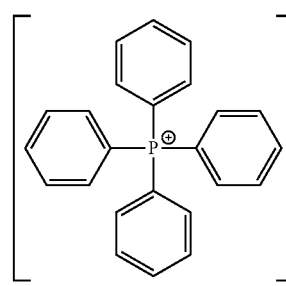

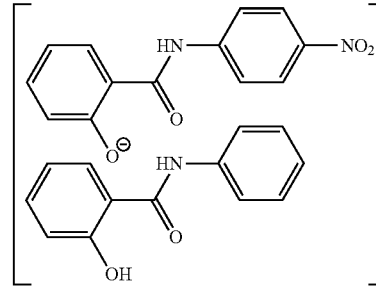

[Fomula 1e]
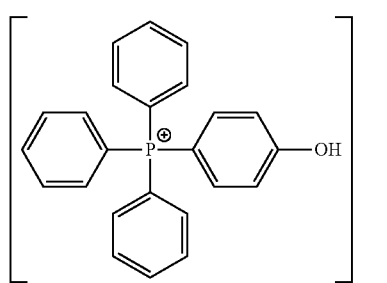
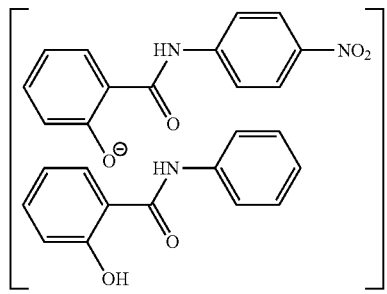
[Formula 1f]
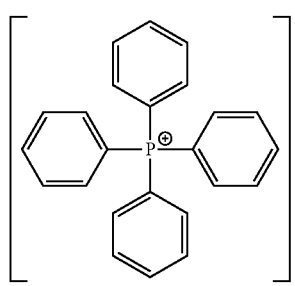
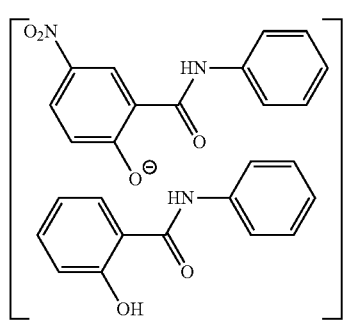
[Formula 1g]
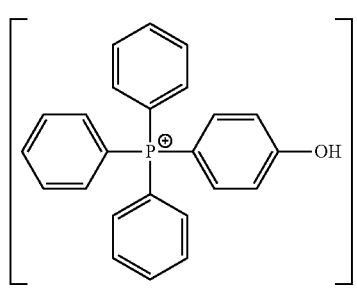
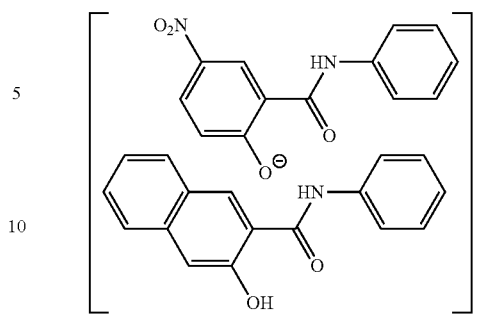
[Formula 1h]
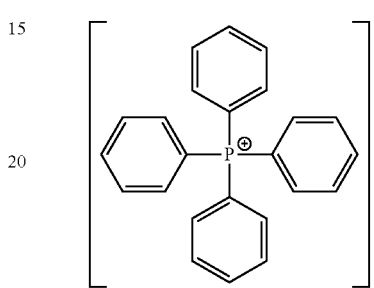
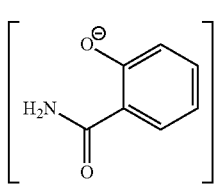
[Formula 1i]
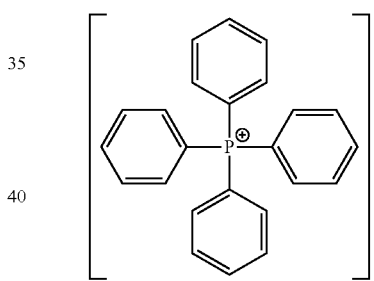
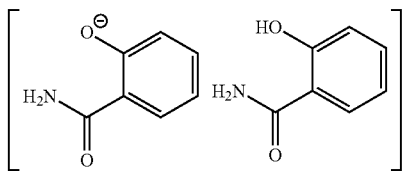
[Formula 1j]
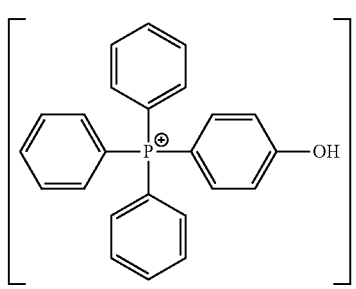

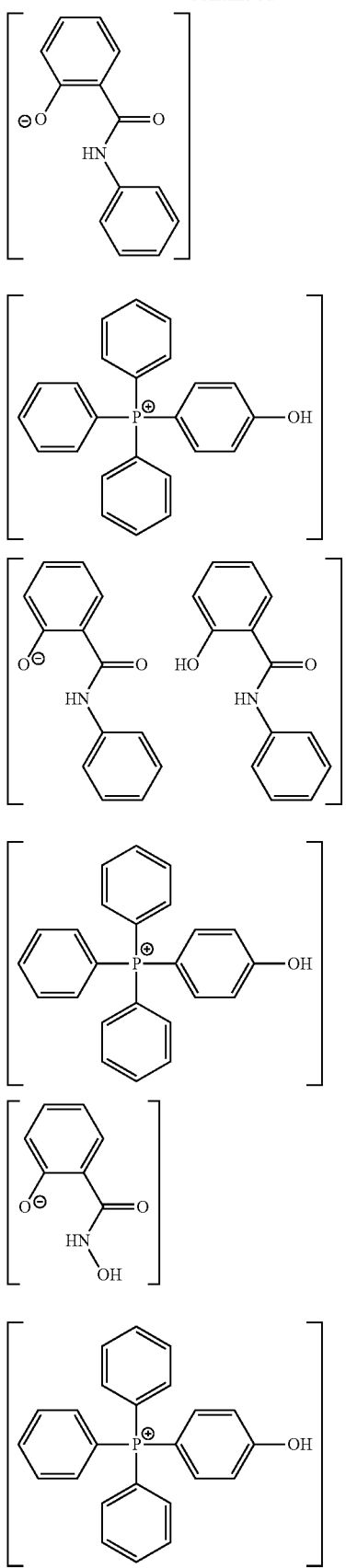

[Formula 1k]

[Formula 1l]

[Formula 1m]

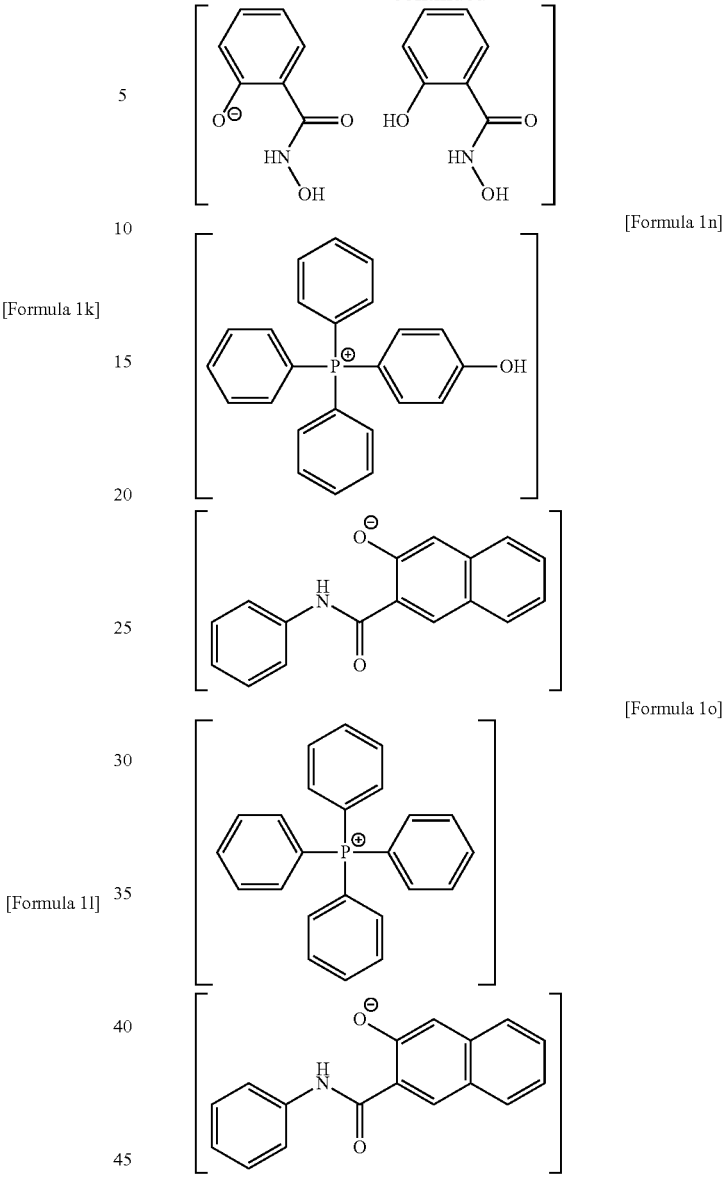

[Formula 1n]

[Formula 1o]

The phosphonium compound according to another embodiment may include a phosphonium cation and an anion having a hydroxyl group and an amide group at the same time. In an implementation, the phosphonium compound may be represented by Formula 2:

[Formula 2]

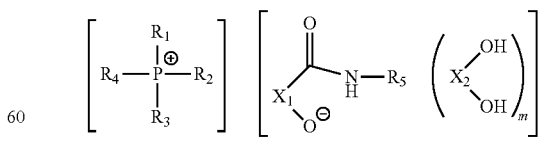

In Formula 2, $R_1$, $R_2$, $R_3$, and $R_4$ may each independently be or include, e.g., a substituted or unsubstituted $C_1$ to $C_{30}$ aliphatic hydrocarbon group, a substituted or unsubstituted $C_6$ to $C_{30}$ aromatic hydrocarbon group, or a substituted or unsubstituted $C_1$ to $C_{30}$ hydrocarbon group including a hetero atom. $X_1$ and $X_2$ may each independently be or include, e.g., a substituted or unsubstituted $C_6$ to $C_{30}$ arylene group, a substituted or unsubstituted $C_3$ to $C_{10}$ cycloalkylene group, or a substituted or unsubstituted $C_1$ to $C_{20}$ alkylene group. $R_5$ may be or include, e.g., hydrogen, a hydroxyl group, a substituted or unsubstituted $C_1$ to $C_{20}$ alkyl group, a substituted or unsubstituted $C_6$ to $C_{30}$ aryl group, a substituted or unsubstituted $C_3$ to $C_{30}$ heteroaryl group, a substituted or unsubstituted $C_3$ to $C_{10}$ cycloalkyl group, a substituted or unsubstituted $C_3$ to $C_{10}$ heterocycloalkyl group, a substituted or unsubstituted $C_7$ to $C_{30}$ arylalkyl group, or a substituted or unsubstituted $C_1$ to $C_{30}$ heteroalkyl group. m may be, e.g., 1 or 2.

In Formula 2, $R_1$, $R_2$, $R_3$, and $R_4$ may each independently be or include, e.g., a substituted or unsubstituted $C_6$ to $C_{30}$ aryl group.

In an implementation, in Formula 2, at least one of $R_1$, $R_2$, $R_3$, and $R_4$ may be substituted with a hydroxyl group.

In an implementation, the phosphonium compound represented by Formula 2 may be represented by one of the following Formulae 2a to 2j.

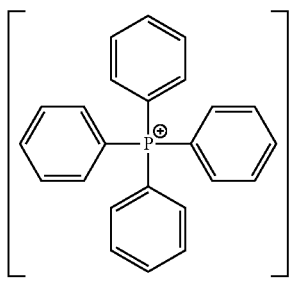

[Formula 2a]

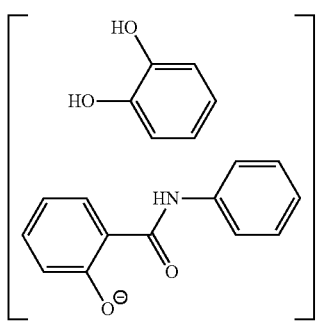

[Formula 2b]

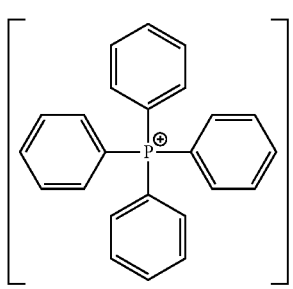

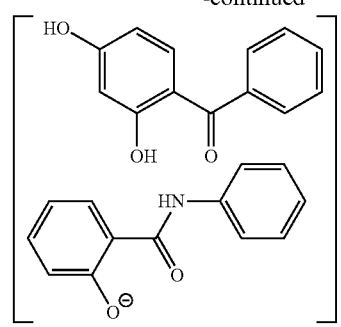

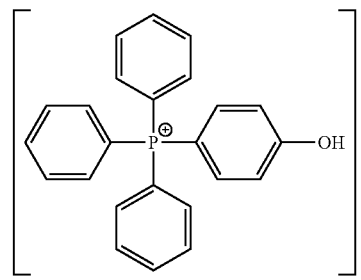

[Formula 2c]

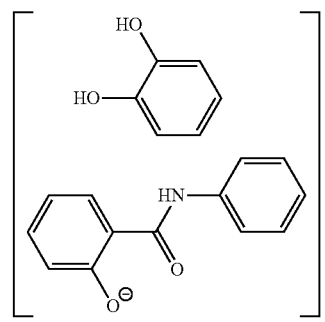

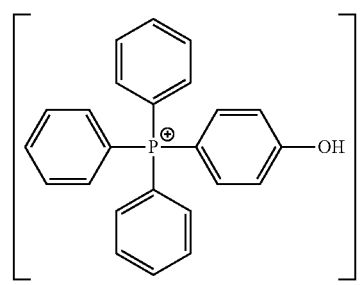

[Formula 2d]

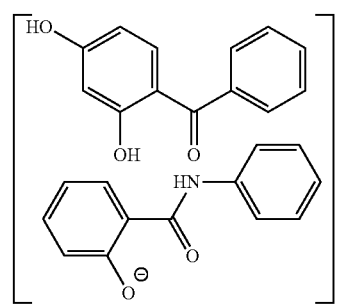

[Formula 2e]
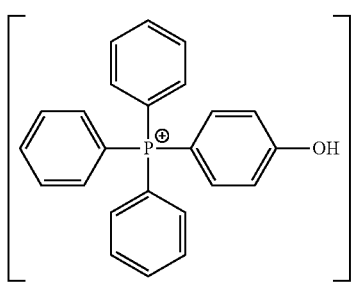
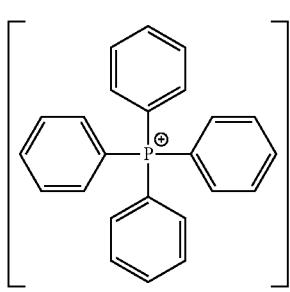
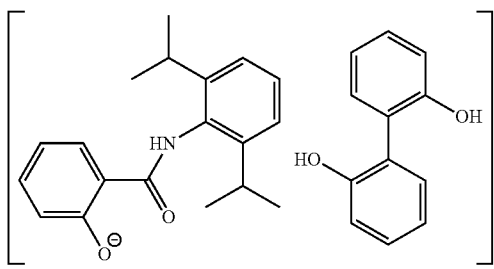
[Formula 2f]
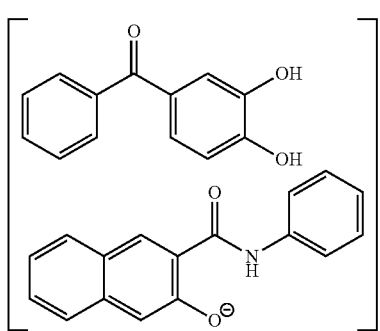
[Formula 2g]
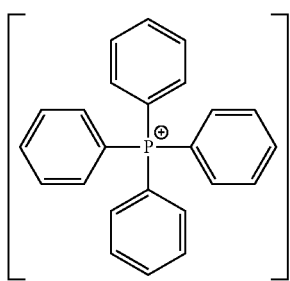
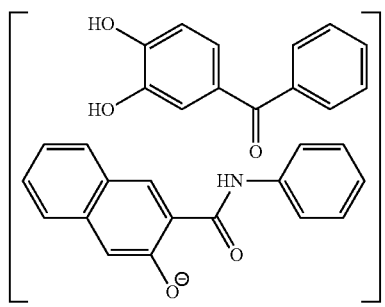
[Formula 2h]
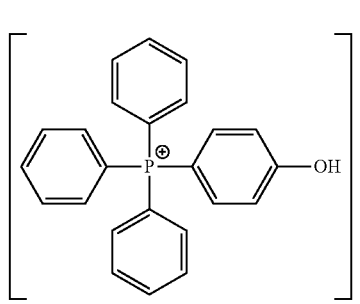
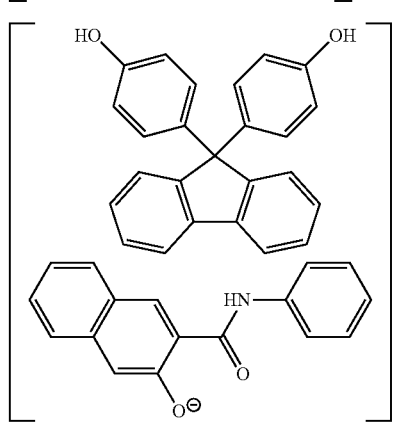
[Formula 2i]
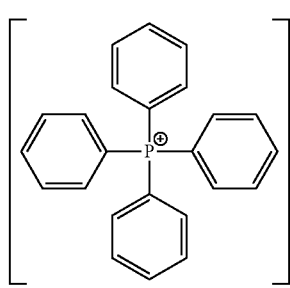
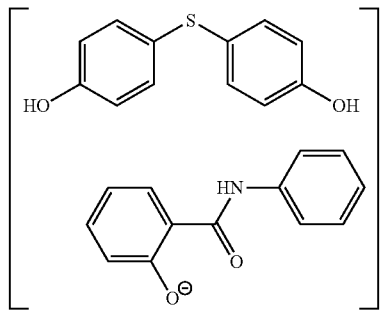

-continued

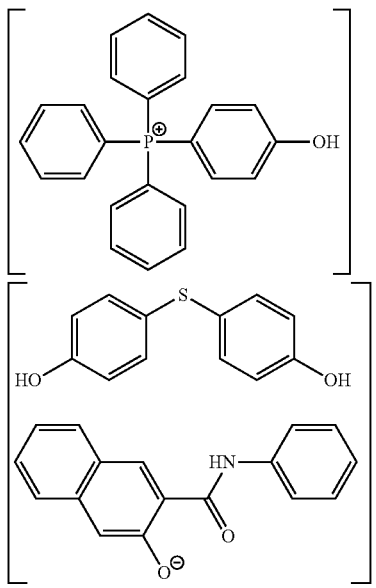

The phosphonium compound may be added to a composition including at least one of an epoxy resin, a curing agent, and inorganic fillers so as to be used as a latent curing catalyst.

A curing reaction may be catalyzed by reaction of a phosphine compound with an epoxide group in an epoxy resin to perform ring opening, followed by reacting with a hydroxyl group in the epoxy resin to perform ring opening of the epoxide group, and then by reaction of a terminal chain of the activated epoxy resin with an epoxide.

The phosphonium compound may provide an epoxy resin composition capable of accelerating curing of an epoxy resin and a curing agent and capable of securing low temperature curability and storage stability while minimizing viscosity change in a mixture including the compound together with an epoxy resin, a curing agent and the like even within desired ranges of time and temperature. Storage stability refers to an activity or condition in which curing is catalyzed only at a desired curing temperature, e.g, without any curing activity at temperature deviating from a desired curing temperature range. As a result, it is possible to store the epoxy resin composition for a long time without viscosity change. Generally, proceeding of curing reaction may cause increase in viscosity and deterioration in flowability when the epoxy resin composition is liquid, and may exhibit viscosity when the epoxy resin composition is solid.

Method for Preparing Phosphonium Compound

The phosphonium compound represented by the Formula 1 may be prepared by, e.g., reacting a phosphonium cation-containing compound represented by Formula 3 with an anilide anion-containing compound represented by Formula 4.

[Formula 3]

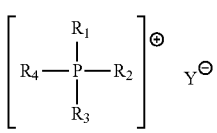

In Formula 3, $R_1$, $R_2$, $R_3$, and $R_4$ may each independently be or include, e.g., a substituted or unsubstituted $C_1$ to $C_{30}$ aliphatic hydrocarbon group, a substituted or unsubstituted $C_6$ to $C_{30}$ aromatic hydrocarbon group, or a substituted or unsubstituted $C_1$ to $C_{30}$ hydrocarbon group including a heteroatom. Y may be, e.g., a halogen.

[Formula 4]

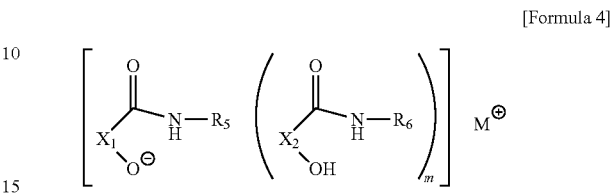

In Formula 4, $X_1$ and $X_2$ may each independently be or include, e.g., a substituted or unsubstituted $C_6$ to $C_{30}$ arylene group, a substituted or unsubstituted $C_3$ to $C_{10}$ cycloalkylene group, or a substituted or unsubstituted $C_1$ to $C_{20}$ alkylene group. $R_5$ and $R_6$ may each independently be or include, e.g., hydrogen, a hydroxyl group, a substituted or unsubstituted $C_1$ to $C_{20}$ alkyl group, a substituted or unsubstituted $C_6$ to $C_{30}$ aryl group, a substituted or unsubstituted $C_3$ to $C_{30}$ heteroaryl group, a substituted or unsubstituted $C_3$ to $C_{10}$ cycloalkyl group, a substituted or unsubstituted $C_3$ to $C_{10}$ heterocycloalkyl group, a substituted or unsubstituted $C_7$ to $C_{30}$ arylalkyl group, or a substituted or unsubstituted $C_1$ to $C_{30}$ heteroalkyl group. m may be, e.g., an integer of 0 to 5. M may be, e.g., an alkali metal or silver (Ag).

The phosphonium compound represented by Formula 2 may be prepared by, e.g., reacting a phosphonium cation-containing compound represented by Formula 3 with an anilide anion-containing compound represented by Formula 5.

[Formula 5]

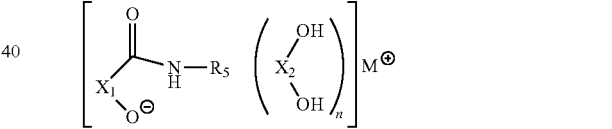

In Formula 5, $X_1$ and $X_2$ may each independently be or include, e.g., a substituted or unsubstituted $C_6$ to $C_{30}$ arylene group, a substituted or unsubstituted $C_3$ to $C_{10}$ cycloalkylene group, or a substituted or unsubstituted $C_1$ to $C_{20}$ alkylene group. $R_5$ may be or include, e.g., hydrogen, a hydroxyl group, a substituted or unsubstituted $C_1$ to $C_{20}$ alkyl group, a substituted or unsubstituted $C_6$ to $C_{30}$ aryl group, a substituted or unsubstituted $C_3$ to $C_{30}$ heteroaryl group, a substituted or unsubstituted $C_3$ to $C_{10}$ cycloalkyl group, a substituted or unsubstituted $C_3$ to $C_{10}$ heterocycloalkyl group, a substituted or unsubstituted $C_7$ to $C_{30}$ arylalkyl group, or a substituted or unsubstituted $C_1$ to $C_{30}$ heteroalkyl group. n may be, e.g., 1 or 2. M may be, e.g., an alkali metal or Ag.

In Formula 3, Y may be, e.g., fluorine, chlorine, bromine or iodine. In Formulae 4 and 5, the alkali metal may be, e.g., lithium, sodium, potassium, rubidium, cesium, francium, or the like.

The phosphonium cation-containing compound may be prepared by reacting a phosphine compound with an organic halide in the presence of a solvent. The organic halide may include, e.g., an alkyl halide, an aryl halide, or an aralkyl halide.

Examples of the phosphine compound may include triphenylphosphine, methyldiphenylphosphine, dimethylphenylphosphine, ethyldiphenylphosphine, diphenylpropylphosphine, isopropyldiphenylphosphine, and diethylphenylphosphine.

The reaction between phosphonium cation-containing compound and the anilide anion-containing compound may be performed in an organic solvent, e.g., methanol, methylene chloride, acetonitrile, N,N-dimethylformamide, or toluene.

The phosphonium cation-containing compound and the anilide anion-containing compound may be reacted in a mole ratio of, e.g., about 1:1 to about 1:6. Reaction between a phosphine compound and an organic halide may produce the phosphonium cation-containing compound, which may be added to an anilide anion-containing compound without an additional separation process.

The anion-containing compound may exhibit good flowability when two molecules form an anion via hydrogen bonding clusters. For example, when two molecules form hydrogen bonding clusters, anions form a stronger bond with cations, thereby suppressing reactivity of the anion-containing compound. Then, as weak hydrogen bonds are rapidly broken, the cation catalyst system may participate in a reaction, thereby allowing the anion-containing compound to exhibit rapid curability.

Epoxy Resin Composition.

The epoxy resin composition according to an embodiment may include the phosphonium compound. In an implementation, the epoxy resin composition may include, e.g., at least one of an epoxy resin, a curing agent, inorganic filler, and a curing catalyst. The curing catalyst may include, e.g., the phosphonium compound represented by Formula 1 or 2.

Epoxy Resin

The epoxy resin may have two or more epoxy groups per molecule. Examples of epoxy resins may include bisphenol A type epoxy resins, bisphenol F type epoxy resins, phenol novolac type epoxy resins, tert-butyl catechol type epoxy resins, naphthalene type epoxy resins, glycidyl amine type epoxy resins, cresol novolac type epoxy resins, biphenyl type epoxy resins, linear aliphatic epoxy resins, cycloaliphatic epoxy resins, heterocyclic epoxy resins, spiro ring-containing epoxy resins, cyclohexane dimethanol type epoxy resins, trimethylol type epoxy resins, and halogenated epoxy resins. These epoxy resins may be used alone or in combination thereof. For example, the epoxy resins may have two or more epoxy groups and one or more hydroxyl groups per molecule. The epoxy resins may include at least one of solid phase epoxy resins and liquid phase epoxy resins. In an implementation, the solid phase epoxy resin may be used.

In an implementation, the epoxy resin may include a biphenyl type epoxy resin represented by Formula 6.

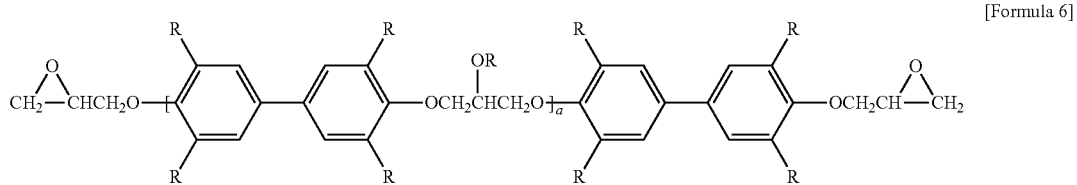

[Formula 6]

In Formula 6, R may be, e.g., a substituted or unsubstituted $C_1$ to $C_4$ alkyl group, and a on average may be 0 to 7.

The composition may include the epoxy resin in an amount of about 2 wt % to about 17 wt %, e.g., about 3 wt % to about 15 wt %, or about 3 wt % to about 12 wt %, in terms of solid content. Within this range, the composition may secure curability.

Curing Agent

The curing agent may include, e.g., phenolaralkyl type phenol resins, phenol novolac type phenol resins, xyloc type phenol resins, cresol novolac type phenol resins, naphthol type phenol resins, terpene type phenol resins, multifunctional phenol resins, dicyclopentadiene-based phenol resins, novolac type phenol resins synthesized from bisphenol A and resol, polyhydric phenol compounds (including tris (hydroxyphenyl)methane and dihydroxybiphenyl), acid anhydrides (including maleic anhydride and phthalic anhydride), and aromatic amines (including meta-phenylenediamine, diaminodiphenylmethane, diaminodiphenylsulfone, and the like). In an implementation, the curing agent may be a phenol resin having one or more hydroxyl groups.

In an implementation, the curing agent may include, e.g., a xyloc type phenol resin represented by Formula 7 and/or a phenolaralkyl type phenol resin represented by Formula 8.

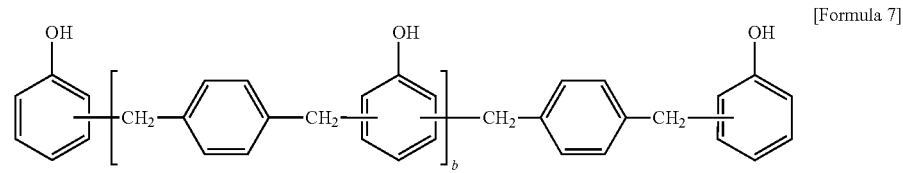

[Formula 7]

In Formula 7, b on average may be, e.g., 0 to 7,

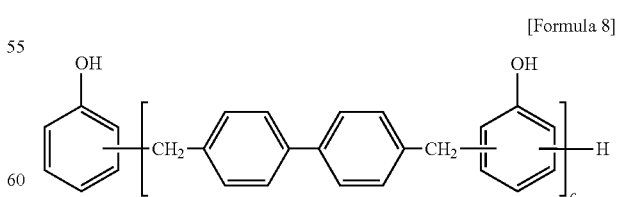

[Formula 8]

In Formula 8, c on average may be, e.g., 1 to 7.

The epoxy resin composition may include the curing agent in an amount of about 0.5 wt % to about 13 wt %, e.g., about 1 wt % to about 10 wt %, or about 2 wt % to 8 wt %, in terms of solid content. Within this range, the composition may secure curability.

Inorganic Filler

The epoxy resin composition may further include inorganic filler. The inorganic filler may help improve mechanical properties of the epoxy resin composition while reducing stress in the epoxy resin composition. Examples of the inorganic filler may include at least one of fused silica, crystalline silica, calcium carbonate, magnesium carbonate, alumina, magnesia, clay, talc, calcium silicate, titanium oxide, antimony oxide, and glass fibers.

Fused silica having a low coefficient of linear expansion may be used with a view toward stress reduction. The fused silica refers to amorphous silica having a specific gravity of 2.3 or less. The fused silica may be prepared by melting crystalline silica or may include amorphous silica products synthesized from various raw materials. The shape and particle diameter of the fused silica may be suitably selected. The inorganic filler may include about 40 wt % to about 100 wt % of a fused silica mixture based on the total weight of the inorganic filler, and the fused silica mixture may include about 50 wt % to about 99 wt % of spherical fused silica having an average particle diameter (volume conversion) of about 5 μm to about 30 μm and about 1 wt % to about 50 wt % of spherical fused silica having an average particle diameter (volume conversion) of about 0.001 μm to about 1 μm. The inorganic fillers may also be adjusted to a maximum particle diameter of about 45 μm, about 55 μm or about 75 μm, depending upon application of the epoxy resin composition. The spherical fused silica may include conductive carbon as a foreign substance on the surface of silica. In an implementation, the spherical fused silica may incorporate a smaller amount of a polar foreign substances.

The inorganic filler may be present in a suitable amount depending upon desired physical properties of the epoxy resin composition, e.g., moldability, low-stress properties, and high-temperature strength. In an implementation, the inorganic filler may be present in an amount of about 70 wt % to about 95 wt %, e.g., about 75% to about 92 wt %, based on the total weight of the epoxy resin composition. Within this range, the epoxy resin composition can secure good flame resistance, flowability, and reliability.

Curing Catalyst

The epoxy resin composition may include a curing catalyst including a phosphonium compound represented by Formula 1 or 2. In an implementation, the phosphonium compound may be present in an amount of about 0.01 wt % to about 5 wt %, e.g., about 0.02 wt % to about 1.5 wt %, or about 0.05 wt % to about 1.5 wt %, in the epoxy resin composition. Within this range, the epoxy resin composition may secure flowability without delaying time for curing reaction.

The epoxy resin composition may further include a non-phosphonium curing catalyst, e.g., that does not contain phosphonium. Examples of non-phosphonium curing catalysts may include tertiary amines, organometallic compounds, organophosphorus compounds, imidazole, boron compounds, and the like. Examples of tertiary amines may include benzyldimethylamine, triethanolamine, triethylenediamine, diethylaminoethanol, tri(dimethylaminomethyl) phenol, 2,2-(dimethylaminomethyl)phenol, 2,4,6-tris(diaminomethyl)phenol, tri-2-ethyl hexanoate, and the like. Examples of organometallic compounds may include chromium acetylacetonate, zinc acetylacetonate, nickel acetylacetonate, and the like. Examples of organophosphorus compounds may include tris-4-methoxyphosphine, triphenylphosphine, triphenylphosphinetriphenylboran, triphenylphosphine-1,4-benzoquinone adducts, and the like. Examples of imidazoles may include 2-methylimidazole, 2-phenylimidazole, 2-aminoimidazole, 2-methyl-1-vinylimidazole, 2-ethyl-4-methylimidazole, 2-heptadecyl imidazole, and the like. Examples of boron compounds may include triphenylphosphine tetraphenyl borate, tetraphenyl borate, trifluoroborane-n-hexylamine, trifluoroborane monoethylamine, tetrafluoroborane triethylamine, tetrafluoroboraneamine, and the like. In an implementation, it is possible to use 1,5-diazabicyclo[4.3.0]non-5-ene (DBN), 1,8-diazabicyclo[5.4.0]undec-7-ene (DBU), phenol novolac resin salt, and the like. For example, the organophosphorus compounds, the boron compounds, and the amines or imidazole curing accelerators may be used alone or in combination. Adducts obtained by pre-reacting an epoxy resin or a curing agent may be used as curing catalyst.

The phosphonium compound according to an embodiment may be present in an amount of about 10 wt % to about 100 wt %, e.g., about 60 wt % to about 100 wt %, based on a total weight of the curing catalyst. Within this range, the epoxy resin composition may secure flowability without delaying time for curing reaction.

The curing catalyst may be present in an amount of about 0.01 wt % to about 5 wt %, e.g., about 0.02 wt % to about 1.5 wt %, or about 0.05 wt % to about 1.5 wt %, in the epoxy resin composition. Within this range, the epoxy resin composition may secure flowability without delaying time for curing reaction.

The composition according to an embodiment may further include a suitable additive. In an implementation, the additive may include, e.g., at least one of a coupling agent, a release agent, a stress relaxant, a crosslinking enhancer, a leveling agent, and a coloring agent.

The coupling agent may include at least one selected from among epoxysilane, aminosilane, mercaptosilane, alkylsilane, and alkoxysilane. The coupling agent may be present in an amount of about 0.1 wt % to about 1 wt % in the epoxy resin composition.

The release agent may include at least one selected from among paraffin wax, ester wax, higher fatty acids, metal salts of higher fatty acids, natural fatty acids, and natural fatty acid metal salts. The mold release agent may be present in an amount of about 0.1 wt % to about 1 wt % in the epoxy resin composition.

The stress reliever may include at least one selected from among modified silicone oil, silicone elastomers, silicone powder, and silicone resin. When present, the stress reliever may be present in an amount of about 6.5 wt % or less, e.g., about 1 wt % or less, or about 0.1 wt % to about 1 wt %, in the epoxy resin composition. As the modified silicone oil, a suitable silicone polymer having good heat resistance may be used. The modified silicone oil may include about 0.05 wt % to about 1.5 wt % of a silicone oil mixture based on the total weight of the epoxy resin composition, wherein the mixture includes at least one selected from the group of silicone oil having an epoxy functional group, silicone oil having an amine functional group, silicone oil having a carboxyl functional group, and a combination thereof. Maintaining amount of the silicone oil is at about 1.5 wt % or less may help reduce and/or prevent the occurrence of surface contamination and lengthy resin bleed. Maintaining the amount of the silicone oil at about 0.05 wt % or greater may help ensure that sufficiently low modulus of elasticity is obtained. In an implementation, the silicone powder may have an average particle diameter of about 15 μm, e.g., because the powder may not deteriorate moldability. When present, the silicone powder may be present in an amount of about 5 wt % or less, e.g., about 0.1 wt % to about 5 wt %, based on the total weight of the epoxy resin composition.

The additive may be present in an amount of about 0.1 wt % to about 10 wt %, e.g., about 0.1 wt % to about 3 wt %, in the epoxy resin composition.

The epoxy resin composition may be curable at low temperature. For example, a curing initiation temperature may be about 90° C. to about 120° C. Within this range, the epoxy resin composition may be cured at low temperature, thereby securing curing at low temperature.

The epoxy resin composition may have a flow length of about 59 to about 77 inches as measured using a transfer molding press at 175° C. under a load of 70 kgf/cm$^2$ in accordance with EMMI-1-66. Within this range, the epoxy resin composition may be used for desired applications.

The epoxy resin composition may have a curing shrinkage rate of less than about 0.4%, e.g., about 0.01% to about 0.39%, as calculated according to Equation 1. Within this range, the curing shrinkage rate may be low and the epoxy resin composition can be used for desired applications.

$$\text{Curing shrinkage} = |C-D|/C \times 100 \quad \text{[Equation 1]}$$

In Equation 1, C is the length of a specimen obtained by transfer molding of an epoxy resin composition at 175° C. under a load of 70 kgf/cm$^2$, and D is the length of the specimen after post-curing the specimen at 170° C. to 180° C. for 4 hours and cooling.

Within this range, the curing shrinkage rate is low and the epoxy resin composition can be used for desired applications.

The epoxy resin composition may have storage stability of about 80% or more as calculated according to Equation 2.

$$\text{Storage stability} = (F1-F0)/F0 \times 100,$$

In Equation 2, F1 is the flow length (inches) of the epoxy resin composition measured after storing the composition at 25° C./50% RH for 72 hours using a transfer molding press at 175° C. and 70 kgf/cm$^2$ in accordance with EMMI-1-66, and F0 is the initial flow length (inches) of the epoxy resin composition.

In the epoxy resin composition, the epoxy resin may be used alone or in the form of adducts, such as a melt master batch, obtained by pre-reacting the epoxy resin with an additive, such as a curing agent, a curing catalyst, a release agent, a coupling agent, and a stress reliever. In an implementation, the epoxy resin composition may be prepared by uniformly mixing all components of the resin composition using a suitable mixer, such as a Henschel mixer or a Redige mixer, followed by melt-kneading in a roll mill or a kneader at about 90° C. to about 120° C., cooling, and pulverizing.

The epoxy resin composition according to an embodiment may be used in a broad range of applications suitable for such an epoxy resin composition in encapsulation of semiconductor devices, adhesive films, insulating resin sheets such as prepregs and the like, circuit substrates, solder resists, underfills, die bonding materials, and component replenishing resins.

Encapsulation of Semiconductor Device

The epoxy resin composition according to an embodiment may be used to encapsulate a semiconductor device, and include an epoxy resin, a curing agent, a phosphonium compound-containing curing catalyst, inorganic fillers, and additives.

A semiconductor device according to an embodiment may be encapsulated with the epoxy resin composition.

FIG. 1 illustrates a cross sectional view of a semiconductor device according to an embodiment. Referring to FIG. 1, a semiconductor device 100 according to an embodiment may include a wiring board 10, bumps 30 formed on the wiring board 10, and a semiconductor chip 20 formed on the bumps 30. A gap between the wiring board 10 and the semiconductor chip 20 may be encapsulated with (e.g., by curing) an epoxy resin composition to form an encapsulant 40. The epoxy resin composition may be an epoxy resin composition according to an embodiment.

Figure 2:
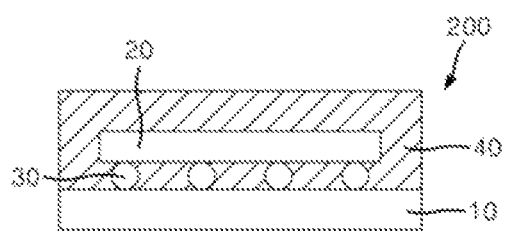
FIG. 2 illustrates a cross sectional view of a semiconductor device of another embodiment.

FIG. 2 illustrates a cross sectional view of a semiconductor device of another embodiment. Referring to FIG. 2, a semiconductor device 200 according to another embodiment may include a wiring board 10, bumps 30 formed on the wiring board 10, and a semiconductor chip 20 formed on the bumps 30. A gap between the wiring board 10 and the semiconductor chip 20 and an entirety of a top surface of the semiconductor chip 20 may be encapsulated with (e.g., by curing) an epoxy resin composition to form an encapsulant 40. The epoxy resin composition may be an epoxy resin composition according to an embodiment.

In FIGS. 1 and 2, the size of each wiring board, bump and semiconductor chip, and the numbers of the bumps are optional and may be modified.

The semiconductor device may be encapsulated with the epoxy resin composition by, e.g., low-pressure transfer molding. In an implementation, the semiconductor device may be molded by, e.g., injection molding, casting, or the like. The semiconductor device that may be fabricated by such a molding process may include, e.g., a copper lead frame, an iron lead frame, an iron lead frame pre-plated with at least one metal selected from among nickel, copper and palladium, or an organic laminate frame.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

PREPARATIVE EXAMPLE 1

Preparation of Phosphonium Compound Represented by Formula 1a 27.2 g of 2-hydroxy-5-nitro-N-p-tolylbenzamide was added to 100 g of MeOH/DMF (weight ratio 1:1), followed by adding 21.6 g of 25 wt % sodium methoxide solution, which in turn was completely dissolved while reacting at ambient temperature for 30 minutes. To the solution, 21.3 g of salicylanilide was added and dissolved, followed by slowly adding 41.9 g of tetraphenylphosphonium bromide previously dissolved in 50 g of methanol. The mixture was allowed to further react for 1 hour. The resulting white solid was filtered to obtain 68.4 g of a compound. The compound was identified by NMR data as a compound represented by Formula 1a:

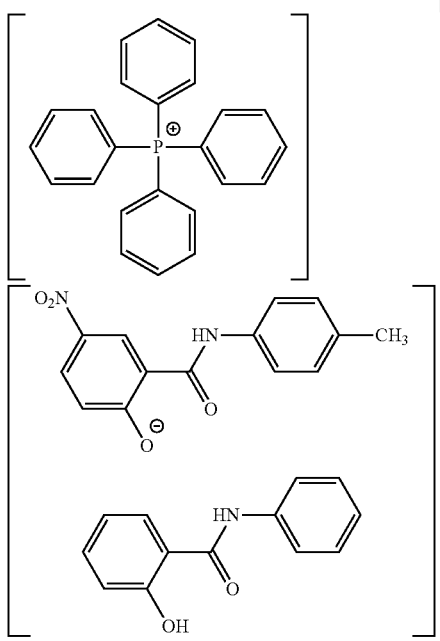

[Formula 1a]

$^1$H NMR (300 MHz, DMSO) δ 13.84 (s, 1H), 11.85 (s, 1H), 10.43 (s, 1H), 8.72 (d, J=3.3 Hz, 1H), 8.03-7.90 (m, 5H), 7.88-7.66 (m, 19H), 7.56 (d, J=8.4 Hz, 2H), 7.49-7.32 (m, 3H), 7.22-7.06 (m, 3H), 7.04-6.90 (m, 2H), 6.32 (d, J=9.4 Hz, 1H), 2.26 (s, 3H).

In the compound represented by Formula 1a, phosphonium, salicylanilide, and a salicylanilide derivative corresponding to an anionic part were found to be present in a ratio of 1:1:1 through integration of the $^1$H NMR spectrum. When salicylanilide was used in an amount exceeding 2 equivalent weights, phosphonium, salicylanilide, and salicylamide were found to maintain the ratio of 1:1:1 through integration of the $^1$H NMR spectrum. Therefore, it was determined that the structure represented by Formula 1a was a stable form.

Preparative Example 2

Preparation of Phosphonium Compound Represented by Formula 1b

To a 1 L round bottom flask, 100 g of triphenylphosphine, 60 g of 4-bromophenol, and 3.7 g of NiBr$_2$ were introduced, followed by adding 130 g of ethylene glycol, and then reacted at 180° C. for 6 hours, thereby obtaining a phosphonium bromide salt represented by Formula 1b' having a substituted phenol:

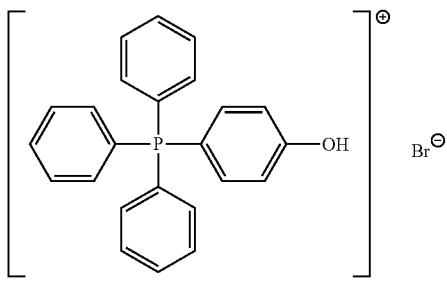

[Formula 1b']

27.2 g of 2-hydroxy-5-nitro-N-p-tolylbenzamide was added to 100 g of MeOH/DMF (weight ratio 1:1), followed by adding 21.6 g of 25 wt % sodium methoxide solution, which in turn was completely dissolved while reacting at ambient temperature for 30 minutes. To the solution, 21.3 g of salicylanilide was added and dissolved, followed by slowly adding 43.5 g of the phosphonium bromide (salt) represented by Formula 1b' previously dissolved in 50 g of methanol. The mixture was allowed to further react for 1 hour. The resulting white solid was filtered to obtain 69.4 g of a compound. The compound was identified by NMR data as a compound represented by Formula 1b:

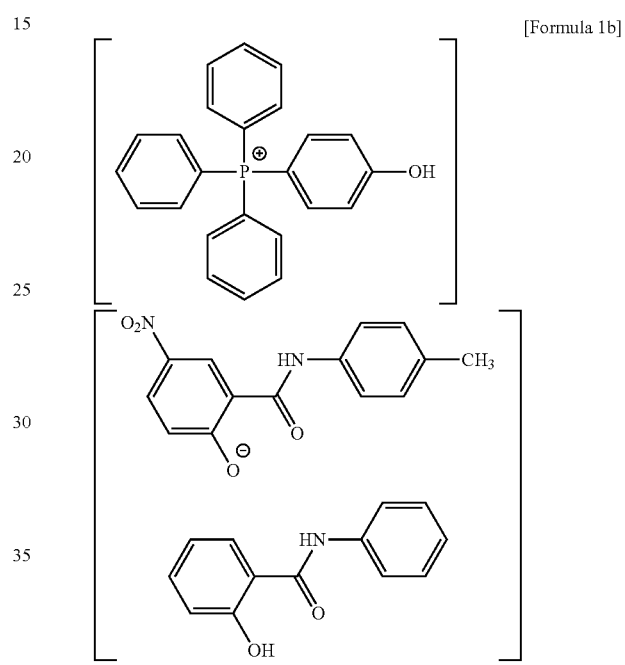

[Formula 1b]

$^1$H NMR (300 MHz, DMSO) δ 13.84 (s, 1H), 11.53 (s, 2H), 10.47 (s, 1H), 8.72 (d, J=3.3 Hz, 1H), 8.02-7.32 (m, 27H), 7.20-7.06 (m, 5H), 6.97 (ddd, J=11.3, 6.5, 2.3 Hz, 2H), 6.33 (d, J=9.4 Hz, 1H), 2.26 (s, 3H).

In the compound represented by Formula 1b, phosphonium, and salicylanilide, and a salicylanilide derivative corresponding to an anionic part were found to be present in a ratio of 1:1:1 through integration of the $^1$H NMR spectrum. When salicylanilide was used in an amount exceeding 2 equivalent weights, phosphonium, salicylanilide, and salicylamide were found to maintain the ratio of 1:1:1 through integration of the $^1$H NMR spectrum. Therefore, it was determined that the structure represented by Formula 1b was a stable form.

Preparative Example 3

Preparation of Phosphonium Compound Represented by Formula 1c 31.3 g of 3-hydroxy N-naphthyl 2-naphthamide was added to 100 g of MeOH/DMF (weight ratio 1:1), followed by adding 21.6 g of 25 wt % sodium methoxide solution, which in turn was completely dissolved while reacting at room temperature for 30 minutes. To the solution, 21.3 g of salicylanilide was added and dissolved, followed by slowly adding 41.9 g of tetraphenylphosphonium bromide previously dissolved in 50 g of methanol. The mixture was allowed to further react for 1 hour. The resulting yellow solid was filtered to obtain 70.4 g of a compound. The compound was identified by NMR data as a compound represented by Formula 1c:

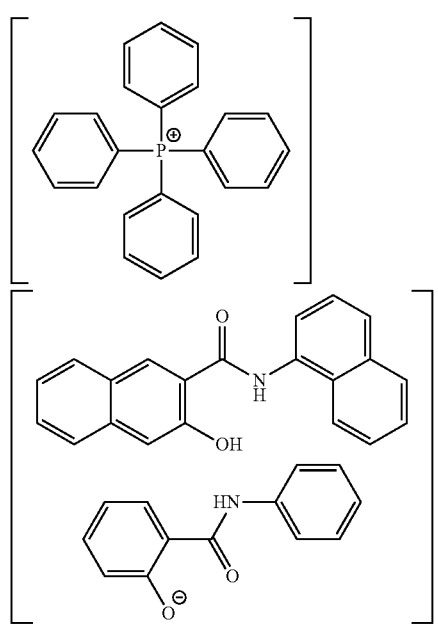

[Formula 1c]

$^1$H NMR (300 MHz, DMSO) δ 11.90 (s, 1H), 8.60-8.40 (m, 3H), 8.04-7.62 (m, 25H), 7.61-7.42 (m, 4H), 7.40-7.16 (m, 4H), 7.07 (t, J=7.3 Hz, 3H), 6.87 (d, J=8.2 Hz, 1H), 6.73 (t, J=7.5 Hz, 1H).

In the compound represented by Formula 1c, phosphonium, and salicylanilide, and a salicylanilide derivative corresponding to an anionic part were found to be present in a ratio of 1:1:1 through integration of the $^1$H NMR spectrum. When salicylanilide was used in an amount exceeding 2 equivalent weights, phosphonium, salicylanilide, and salicylamide were found to maintain the ratio of 1:1:1 through integration of the $^1$H NMR spectrum. Therefore, it was determined that the structure represented by Formula 1c was a stable form.

Preparative Example 4

Preparation of Phosphonium Compound Represented by Formula 1d 25.8 g of 4'-nitrosalicylanilide was added to 100 g of MeOH/DMF (weight ratio 1:1), followed by adding 21.6 g of 25 wt % sodium methoxide solution, which in turn was completely dissolved while reacting at ambient temperature for 30 minutes. To the solution, 21.3 g of salicylanilide was added and dissolved, followed by slowly adding 41.9 g of tetraphenylphosphonium bromide previously dissolved in 50 g of methanol. The mixture was allowed to further react for 1 hour. The resulting yellow solid was filtered to obtain 71.8 g of a compound. The compound was identified by NMR data as a compound represented by Formula 1d:

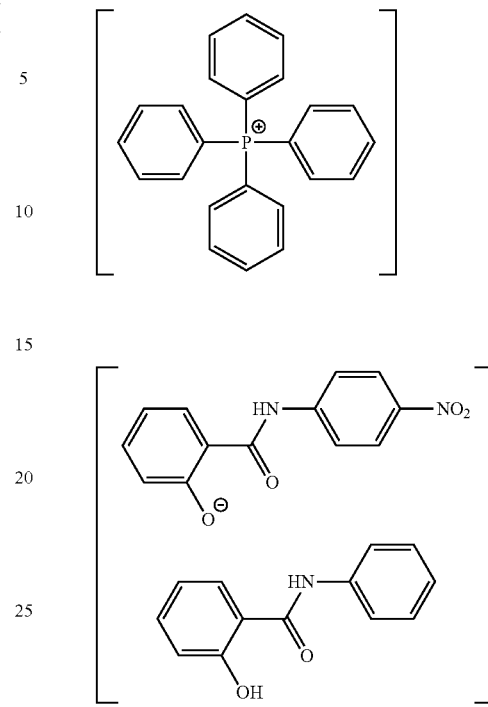

[Formula 1d]

$^1$H NMR (300 MHz, DMSO) δ 11.55 (s, 1H), 8.33-8.13 (m, 2H), 8.03-7.87 (m, 7H), 7.87-7.65 (m, 18H), 7.57-7.27 (m, 4H), 7.22-7.03 (m, 2H), 6.94 (d, J=8.2 Hz, 1H), 6.86-6.75 (m, 1H), 6.68 (d, J=8.4 Hz, 1H), 6.46 (t, J=7.4 Hz, 1H).

In the compound represented by Formula 1d, phosphonium, and salicylanilide and a salicylanilide derivative corresponding to an anionic part were found to be present in a ratio of 1:1:1 through integration of the $^1$H NMR spectrum. When salicylanilide was used in an amount exceeding 2 equivalent weights, phosphonium, salicylanilide and salicylamide were found to maintain the ratio of 1:1:1 through integration of the $^1$H NMR spectrum. Therefore, it was determined that the structure represented by Formula 1d was a stable form.

Preparative Example 5

Preparation of Phosphonium Compound Represented by Formula 1e 25.8 g of 4'-nitrosalicylanilide was added to 100 g of MeOH/DMF (weight ratio 1:1), followed by adding 21.6 g of 25 wt % sodium methoxide solution, which in turn was completely dissolved while reacting at ambient temperature for 30 minutes. To the solution, 21.3 g of salicylanilide was added and dissolved, followed by slowly adding 43.5 g of the phosphonium bromide (salt) represented by Formula 1b' previously dissolved in 50 g of methanol. The mixture was allowed to further react for 1 hour. The resulting yellow solid was filtered to obtain 72.7 g of a compound. The compound was identified by NMR data as a compound represented by Formula 1e:

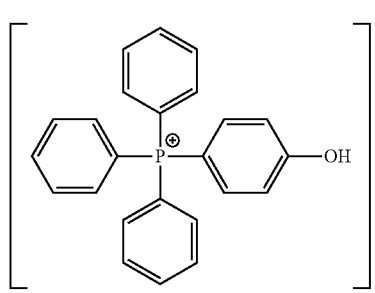

[Formula 1e]

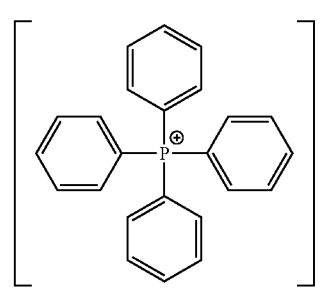

[Formula 1f]

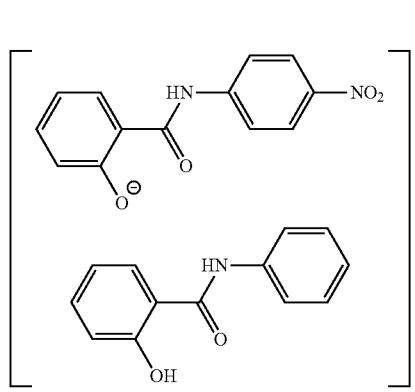

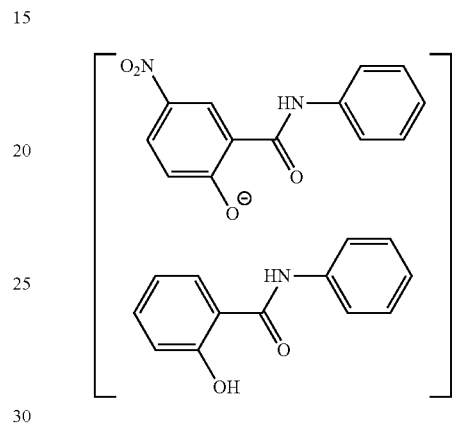

¹H NMR (300 MHz, DMSO) δ 11.44 (s, 1H), 8.30-8.12 (m, 2H), 7.99-7.84 (m, 6H), 7.84-7.61 (m, 14H), 7.43 (ddd, J=8.1, 6.0, 5.2 Hz, 3H), 7.39-7.29 (m, 3H), 7.25-7.15 (m, 1H), 7.11 (dt, J=14.8, 5.3 Hz, 3H), 6.94 (d, J=8.2 Hz, 1H), 6.87-6.66 (m, 2H), 6.53 (t, J=7.4 Hz, 1H).

In the compound represented by Formula 1e, phosphonium, and salicylanilide and a salicylanilide derivative corresponding to an anionic part were found to be present in a ratio of 1:1:1 through integration of the ¹H NMR spectrum. When salicylanilide was used in an amount exceeding 2 equivalent weights, phosphonium, salicylanilide and salicylamide were found to maintain the ratio of 1:1:1 through integration of the ¹H NMR spectrum. Therefore, it was determined that the structure represented by Formula 1e was a stable form.

Preparative Example 6

Preparation of Phosphonium Compound Represented by Formula 1f 25.8 g of 2-hydroxy 5-nitrobenzanilide was added to 100 g of MeOH/DMF (weight ratio 1:1), followed by adding 21.6 g of 25 wt % sodium methoxide solution, which in turn was completely dissolved while reacting at ambient temperature for 30 minutes. To the solution, 21.3 g of salicylanilide was added and dissolved, followed by slowly adding 41.9 g of tetraphenylphosphonium bromide previously dissolved in 50 g of methanol. The mixture was allowed to further react for 1 hour. The resulting yellow solid was filtered to obtain 67.9 g of a compound. The compound was identified by NMR data as a compound represented by Formula 1f:

¹H NMR (300 MHz, DMSO) δ 13.94 (s, 1H), 11.86 (s, 1H), 10.42 (s, 1H), 8.73 (d, J=3.3 Hz, 1H), 8.11-7.90 (m, 5H), 7.90-7.62 (m, 20H), 7.57-7.25 (m, 5H), 7.20-7.08 (m, 1H), 7.08-6.91 (m, 3H), 6.34 (d, J=9.4 Hz, 1H).

In the compound represented by Formula 1f, phosphonium, and salicylanilide and a salicylanilide derivative corresponding to an anionic part were found to be present in a ratio of 1:1:1 through integration of the ¹H NMR spectrum. When salicylanilide was used in an amount exceeding 2 equivalent weights, phosphonium, salicylanilide and salicylamide were found to maintain the ratio of 1:1:1 through integration of the ¹H NMR spectrum. Therefore, it was determined that the structure represented by Formula 1f was a stable form.

Preparative Example 7

Preparation of Phosphonium Compound Represented by Formula 1g 25.8 g of 2-hydroxy 5-nitrobenzanilide was added to 100 g of MeOH/DMF (weight ratio 1:1), followed by adding 21.6 g of 25 wt % sodium methoxide solution, which in turn was completely dissolved while reacting at ambient temperature for 30 minutes. To the solution, 21.3 g of salicylanilide was added and dissolved, followed by slowly adding 43.5 g of the phosphonium bromide (salt) represented by Formula 1b' previously dissolved in 50 g of methanol. The mixture was allowed to further react for 1 hour. The resulting yellow solid was filtered to obtain 68.8 g of a compound. The compound was identified by NMR data as a compound represented by Formula 1g:

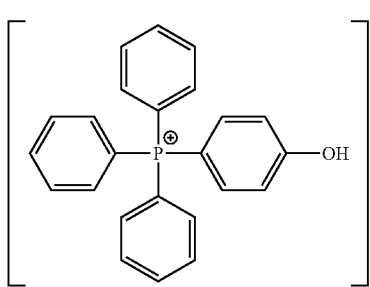

[Formula 1g]

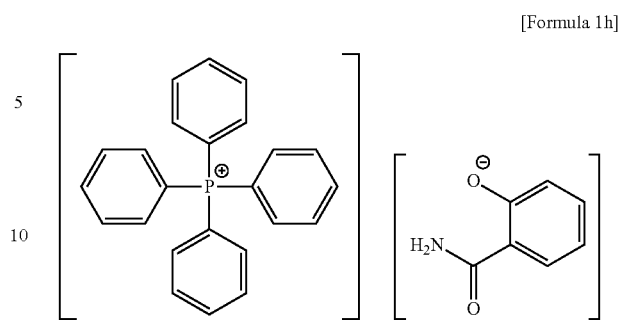

[Formula 1h]

$^1$H NMR δ 8.00-7.94 (4H, dt), 7.85-7.70 (17H, m), 7.29 (1H, dt), 6.82 (1H, d), 6.72 (1H, t)

Preparative Example 9

Preparation of Phosphonium Compound Represented by Formula 1i 27.4 g of salicylamide was added to 50 g of MeOH, followed by adding 21.6 g of 25 wt % sodium methoxide solution, which in turn was completely dissolved while reacting at ambient temperature for 30 minutes. To the solution, a solution of 41.9 g of tetraphenylphosphonium bromide previously dissolved in 50 g of methanol was slowly added. The mixture was allowed to further react for 1 hour. The resulting white solid was filtered to obtain 50.8 g of a compound. The compound was identified by NMR data as a compound represented by Formula 1i:

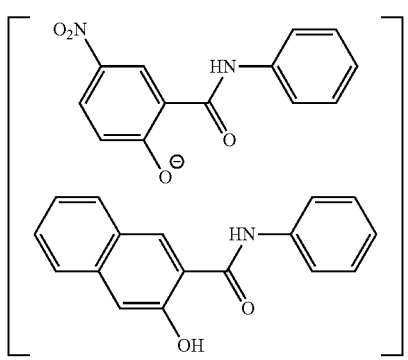

$^1$H NMR (300 MHz, DMSO) δ 13.94 (s, 1H), 10.70 (s, 1H), 8.73 (d, J=3.3 Hz, 1H), 8.51 (s, 1H), 7.94 (ddt, J=6.8, 3.3, 1.5 Hz, 4H), 7.88-7.62 (m, 18H), 7.58-7.45 (m, 3H), 7.44-7.26 (m, 6H), 7.15 (dq, J=4.6, 1.4 Hz, 3H), 7.07-6.95 (m, 1H), 6.35 (d, J=9.4 Hz, 1H).

In the compound represented by Formula 1g, phosphonium, and salicylanilide and a salicylanilide derivative corresponding to an anionic part were found to be present in a ratio of 1:1:1 through integration of the $^1$H NMR spectrum. When salicylanilide was used in an amount exceeding 2 equivalent weights, phosphonium, salicylanilide and salicylamide were found to maintain the ratio of 1:1:1 through integration of the $^1$H NMR spectrum. Therefore, it was determined that the structure represented by Formula 1g was a stable form.

Preparative Example 8

Preparation of Phosphonium Compound Represented by Formula 1h 13.7 g of salicylamide was added to 50 g of MeOH, followed by adding 21.6 g of 25 wt % sodium methoxide solution, which in turn was completely dissolved while reacting at ambient temperature for 30 minutes. To the solution, a solution of 41.9 g of tetraphenylphosphonium bromide previously dissolved in 50 g of methanol was slowly added. The mixture was allowed to further react for 1 hour. The resulting white solid was filtered to obtain 41 g of a compound. The compound was identified by NMR data as a compound represented by Formula 1h:

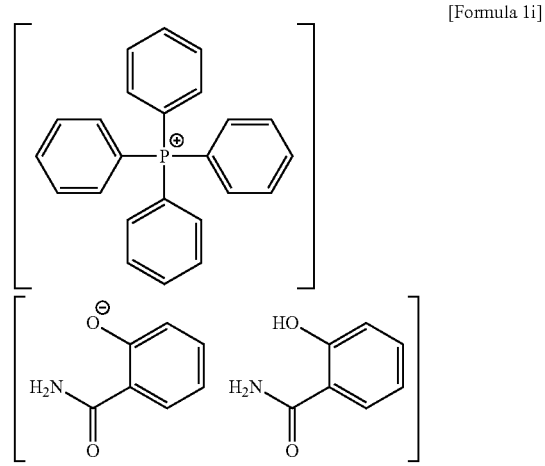

[Formula 1i]

$^1$H NMR δ 8.00-7.94 (4H, dt), 7.85-7.70 (18H, m), 7.33 (2H, dt), 6.85 (2H, d), 6.77 (2H, t)

In the compound represented by Formula 1i, phosphonium and salicylamide corresponding to an anionic part were found to be present in a ratio of 1:2 through integration of the $^1$H NMR spectrum. When salicylamide was used in an amount exceeding 2 equivalent weights, phosphonium and salicylamide were found to maintain a ratio of 1:2 through integration of the $^1$H NMR spectrum. Therefore, it was determined that the structure represented by Formula 1i was a stable form.

Preparative Example 10

Preparation of Phosphonium Compound Represented by Formula 1j 21.3 g of salicylamide was added to 50 g of MeOH, followed by adding 21.6 g of 25 wt % sodium methoxide solution, which in turn was completely dissolved while reacting at ambient temperature for 30 minutes. To the solution, a solution of 43.5 g of the phosphonium bromide (salt) represented by Formula 1b' and having a substituted phenol previously dissolved in 50 g of methanol was slowly added. The mixture was allowed to further react for 1 hour. The resulting white solid was filtered to obtain 47 g of a compound. The compound was identified by NMR data as a compound represented by Formula 1j:

[Formula 1j]

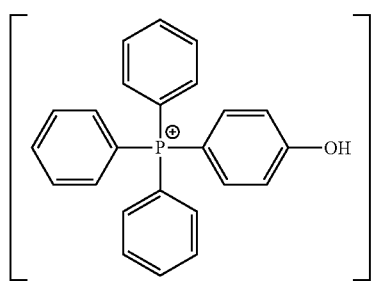

$^1$H NMR δ 7.87 (3H, t), 7.85-7.66 (15H, m), 7.38 (2H, dd), 7.31 (2H, dt), 7.18 (1H, dt), 7.05-6.97 (3H, m), 6.71 (1H, d), 6.54 (1H, t)

Preparative Example 11

Preparation of Phosphonium Compound Represented by Formula 1k 42.6 g of salicylanilide was added to 50 g of MeOH, followed by adding 21.6 g of 25 wt % sodium methoxide solution, which in turn was completely dissolved while reacting at ambient temperature for 30 minutes. To the solution, a solution of 43.5 g of the phosphonium bromide (salt) represented by Formula 1b' and having a substituted phenol previously dissolved in 50 g of methanol was slowly added. The mixture was allowed to further react for 1 hour. The resulting white solid was filtered to obtain 66 g of a compound. The compound was identified by NMR data as a compound represented by Formula 1k:

[Formula 1k]

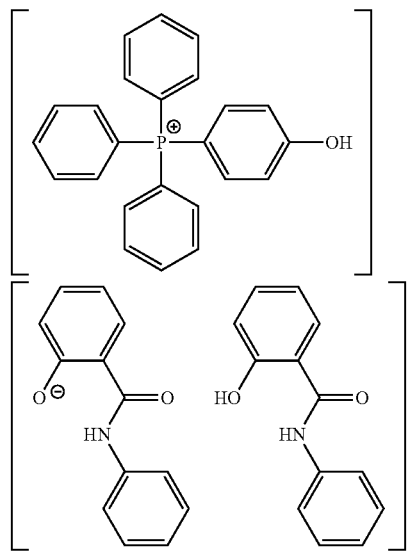

$^1$H NMR δ 7.95-7.87 (5H, m), 7.82-7.66 (16H, m), 7.43 (2H, dd), 7.35 (4H, t), 7.26 (2H, t), 7.08-7.03 (4H, m), 6.85 (2H, dt), 6.67 (2H, dt)

In the compound represented by Formula 1k, phosphonium and salicylamide corresponding to an anionic part were found to be present in a ratio of 1:2 through integration of the $^1$H NMR spectrum. When salicylanilide was used in an amount exceeding 2 equivalent weights, phosphonium and salicylanilide were found to maintain a ratio of 1:2 through integration of the $^1$H NMR spectrum. Therefore, it was determined that the structure represented by Formula 1k was a stable form.

Preparative Example 12

Preparation of Phosphonium Compound Represented by Formula 1l 15.3 g of salicylhydroxamic acid was added to 50 g of MeOH, followed by adding 21.6 g of 25 wt % sodium methoxide solution, which in turn was completely dissolved while reacting at ambient temperature for 30 minutes. To the solution, a solution of 41.9 g of the phosphonium bromide (salt) represented by Formula 1b' and having a substituted phenol previously dissolved in 50 g of methanol was slowly added. The mixture was allowed to further react for 1 hour. The resulting white solid was filtered to obtain 49 g of a compound. The compound was identified by NMR data as a compound represented by Formula 1l:

[Formula 1l]

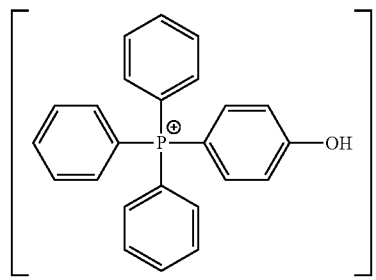

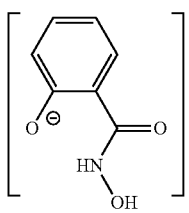

$^1$H NMR δ 7.87 (3H, t), 7.77-7.73 (6H, m), 7.69-7.65 (6H, m), 7.59 (1H, dd), 7.15 (1H, dt), 7.06 (2H, dd), 6.69-6.64 (2H, m), 6.55 (2H, dd)

Preparative Example 13

Preparation of Phosphonium Compound Represented by Formula 1m 30.6 g of salicylhydroxamic acid was added to 50 g of MeOH, followed by adding 21.6 g of 25 wt % sodium methoxide solution, which in turn was completely dissolved while reacting at ambient temperature for 30 minutes. To the solution, a solution of 41.9 g of the phosphonium bromide (salt) represented by Formula 1b' and having a substituted phenol previously dissolved in 50 g of methanol was slowly added. The mixture was allowed to further react for 1 hour. The resulting white solid was filtered to obtain 60 g of a compound. The compound was identified by NMR data as a compound represented by Formula 1m:

[Formula 1m]

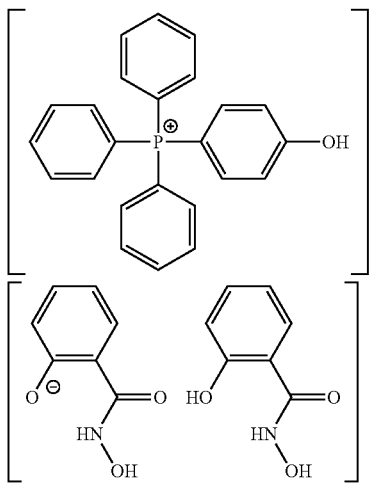

$^1$H NMR δ 7.87 (3H, t), 7.77-7.73 (6H, m), 7.70-7.66 (6H, m), 7.63 (2H, dd), 7.18 (2H, dt), 7.13 (2H, dd), 6.75-6.69 (4H, m), 6.65 (2H, dd)

Preparative Example 14

Preparation of Phosphonium Compound Represented by Formula 1n 26.3 g of 3-hydroxy-2-naphthanilde was added to 50 g of MeOH, followed by adding 21.6 g of 25 wt % sodium methoxide solution, which in turn was completely dissolved while reacting at ambient temperature for 30 minutes. To the solution, a solution of 43.5 g of the phosphonium bromide (salt) represented by Formula 1c' and having a substituted phenol previously dissolved in 50 g of methanol was slowly added. The mixture was allowed to further react for 1 hour. The resulting white solid was filtered to obtain 49 g of a compound. The compound was identified by NMR data as a compound represented by Formula 1n:

[Formula 1n]

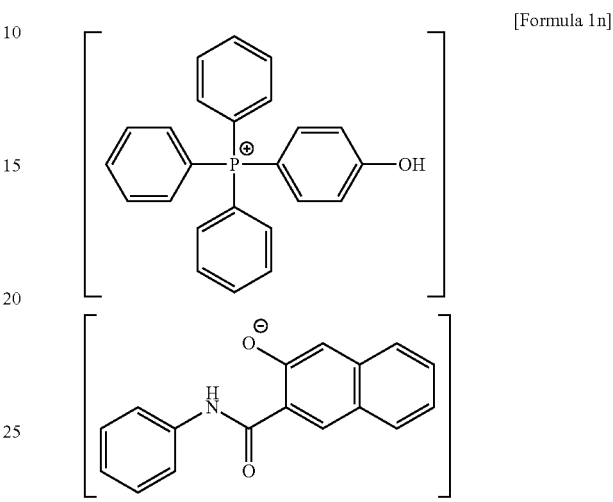

$^1$H NMR δ 8.30 (1H, s), 7.87 (3H, t), 7.79-7.73 (8H, m), 7.69-7.64 (6H, m), 7.57 (1H, d), 7.44 (2H, dd), 7.33-7.27 (3H, m), 7.11 (1H, t), 7.06 (2H, dd), 6.98 (1H, t), 6.82 (1H, t), 6.59 (1H, s)

Preparative Example 15

Preparation of Phosphonium Compound Represented by Formula 1o 26.3 g of 3-hydroxy-2-naphthanilde was added to 50 g of MeOH, followed by adding 21.6 g of 25 wt % sodium methoxide solution, which in turn was completely dissolved while reacting at ambient temperature for 30 minutes. To the solution, a solution of 41.9 g of tetraphenylphosphonium bromide previously dissolved in 50 g of methanol was slowly added. The mixture was allowed to further react for 1 hour. The resulting white solid was filtered to obtain 53 g of a compound. The compound was identified by NMR data as a compound represented by Formula 1o:

[Formula 1o]

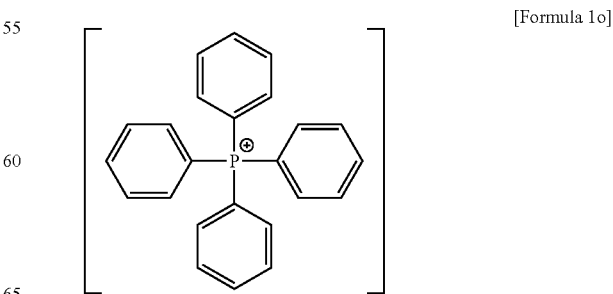

-continued

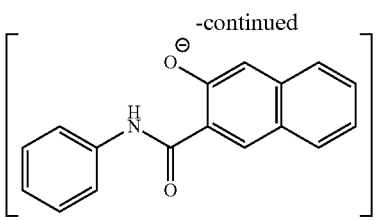

$^1$H NMR δ 8.30 (1H, s), 8.00-7.94 (4H, dt), 7.85-7.70 (18H, m), 7.57 (1H, d), 7.33-7.27 (3H, m), 7.11 (1H, t), 6.98 (1H, t), 6.82 (1H, t), 6.59 (1H, s)

Preparative Example 16

Preparation of Phosphonium Compound Represented by Formula 2a 21.3 g of salicylanilide was added to 100 g of MeOH, followed by adding 21.6 g of 25 wt % sodium methoxide solution, which in turn was completely dissolved while reacting at ambient temperature for 30 minutes. To the solution, 11.0 g of pyrocatechol was added and dissolved, followed by slowly adding 41.9 g of tetraphenylphosphonium bromide previously dissolved in 50 g of methanol. The mixture was allowed to further react for 1 hour. The resulting white solid was filtered to obtain 43.2 g of a compound. The compound was identified by NMR data as a compound represented by Formula 2a:

[Formula 2a]

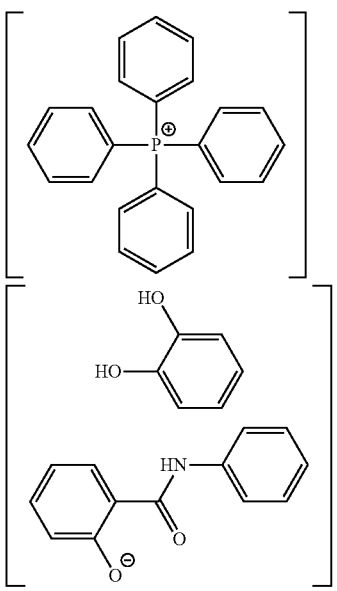

$^1$H NMR (300 MHz, DMSO) δ 14.69 (s, 3H), 8.02-7.90 (m, 8H), 7.87-7.62 (m, 37H), 7.32-7.21 (m, 4H), 7.05-6.89 (m, 4H), 6.55 (ddd, J=11.6, 9.4, 4.5 Hz, 8H), 6.38 (ddd, J=7.9, 2.1, 0.7 Hz, 3H), 6.27 (ddd, J=7.9, 6.9, 1.2 Hz, 2H).

In the compound represented by Formula 2a, phosphonium, salicylanilide and a dihydroxy compound corresponding to an anionic part were found to be present in a ratio of 1:1:1 through integration of the $^1$H NMR spectrum. When salicylanilide was used in an amount exceeding 2 equivalent weights, phosphonium, salicylanilide and pyrocatechol were found to maintain the ratio of 1:1:1 through integration of the $^1$H NMR spectrum. Therefore, it was determined that the structure represented by Formula 2a was a stable form.

Preparative Example 17

Preparation of Phosphonium Compound Represented by Formula 2b 21.3 g of salicylanilide was added to 100 g of MeOH, followed by adding 21.6 g of 25 wt % sodium methoxide solution, which in turn was completely dissolved while reacting at ambient temperature for 30 minutes. To the solution, 21.4 g of 2,4-dihydroxy benzophenone was added and dissolved, followed by slowly adding 41.9 g of tetraphenylphosphonium bromide previously dissolved in 50 g of methanol. The mixture was allowed to further react for 1 hour. The resulting white solid was filtered to obtain 54.4 g of a compound. The compound was identified by NMR data as a compound represented by Formula 2b:

[Formula 2b]

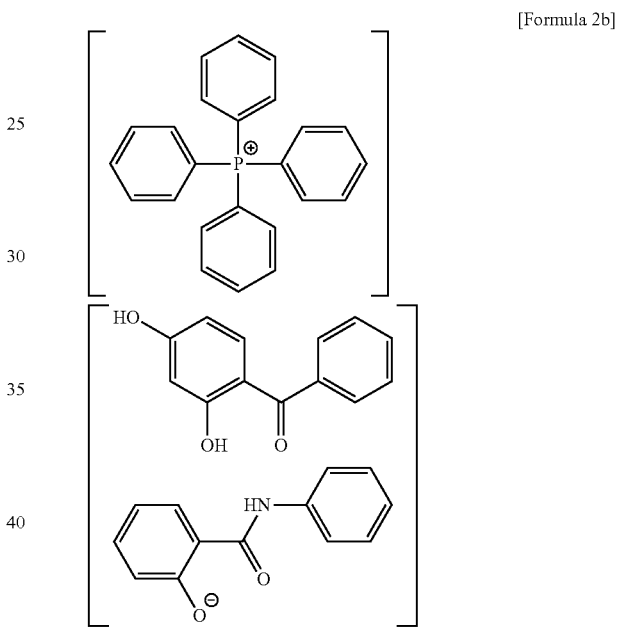

$^1$H NMR (300 MHz, DMSO) δ 13.87 (s, 1H), 12.51 (s, 1H), 8.03-7.90 (m, 4H), 7.88-7.64 (m, 18H), 7.64-7.47 (m, 5H), 7.29 (dd, J=10.9, 5.3 Hz, 3H), 7.09 (ddd, J=8.6, 6.9, 2.0 Hz, 1H), 6.99 (dd, J=10.5, 4.2 Hz, 1H), 6.59 (dd, J=8.3, 1.0 Hz, 1H), 6.44-6.34 (m, 1H), 6.31-6.19 (m, 2H).

In the compound represented by Formula 2b, phosphonium, salicylanilide and a dihydroxy compound corresponding to an anionic part were found to be present in a ratio of 1:1:1 through integration of the $^1$H NMR spectrum. When salicylanilide was used in an amount exceeding 2 equivalent weights, phosphonium, salicylanilide and pyrocatechol were found to maintain the ratio of 1:1:1 through integration of the $^1$H NMR spectrum. Therefore, it was determined that the structure represented by Formula 2b was a stable form.

Preparative Example 18

Preparation of Phosphonium Compound Represented by Formula 2c 21.3 g of salicylanilide was added to 100 g of MeOH, followed by adding 21.6 g of 25 wt % sodium methoxide solution, which in turn was completely dissolved while reacting at ambient temperature for 30 minutes. To the solution, 11.0 g of pyrocatechol was added and dissolved, followed by slowly adding 43.5 g of the phosphenium bromide (salt) represented by Formula 1b' previously dissolved in 50 g of methanol. The mixture was allowed to further react for 1 hour. The resulting white solid was filtered to obtain 48.6 g of a compound. The compound was identified by NMR data as a compound represented by Formula 2c:

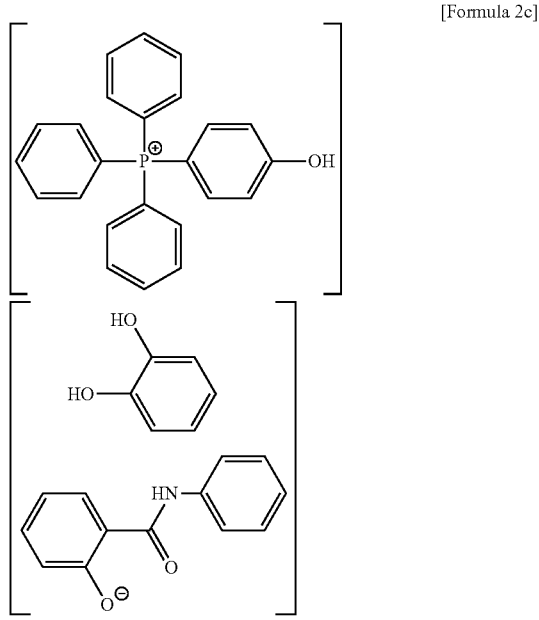

[Formula 2c]

$^1$H NMR (300 MHz, DMSO) δ 13.04 (s, 1H), 8.09-7.82 (m, 4H), 7.73 (ddd, J=27.1, 15.2, 8.2 Hz, 12H), 7.31 (tt, J=23.6, 12.0 Hz, 4H), 7.18 (dd, J=8.0, 7.2 Hz, 1H), 7.00 (dd, J=14.1, 5.4 Hz, 3H), 6.79 (d, J=8.3 Hz, 1H), 6.58 (dd, J=18.6, 9.4 Hz, 3H), 6.38 (d, J=7.9 Hz, 1H).

In the compound represented by Formula 2c, phosphonium, salicylanilide and a dihydroxy compound corresponding to an anionic part were found to be present in a ratio of 1:1:1 through integration of the $^1$H NMR spectrum. When salicylanilide was used in an amount exceeding 2 equivalent weights, phosphonium, salicylanilide and pyrocatechol were found to maintain the ratio of 1:1:1 through integration of the $^1$H NMR spectrum. Therefore, it was determined that the structure represented by Formula 2c was a stable form.

Preparative Example 19

Preparation of Phosphonium Compound Represented by Formula 2d 21.3 g of salicylanilide was added to 100 g of MeOH, followed by adding 21.6 g of 25 wt % sodium methoxide solution, which in turn was completely dissolved while reacting at ambient temperature for 30 minutes. To the solution, 21.4 g of 2,4-dihydroxy benzophenone was added and dissolved, followed by slowly adding 43.5 g of the phosphenium bromide (salt) represented by Formula 1b' previously dissolved in 50 g of methanol. The mixture was allowed to further react for 1 hour. The resulting ivory solid was filtered to obtain 60.9 g of a compound. The compound was identified by NMR data as a compound represented by Formula 2d:

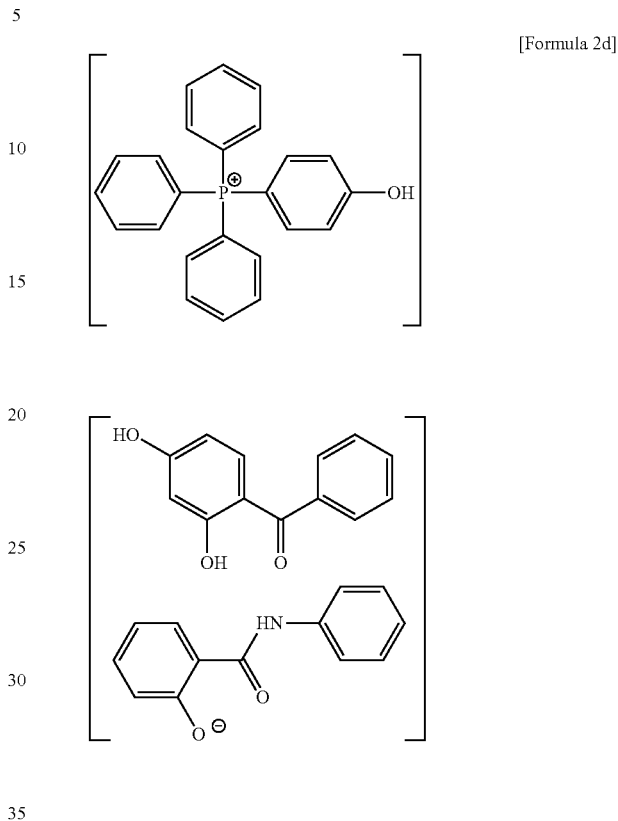

[Formula 2d]

$^1$H NMR (300 MHz, DMSO) δ 12.84 (s, 2H), 8.00-7.44 (m, 22H), 7.28 (dddd, J=10.2, 9.6, 8.7, 5.4 Hz, 6H), 7.09-6.94 (m, 3H), 6.76 (dd, J=8.3, 0.9 Hz, 1H), 6.64-6.52 (m, 1H), 6.31 (dt, J=5.7, 2.2 Hz, 2H).

In the compound represented by Formula 2d, phosphonium, and salicylanilide and a salicylanilide derivative corresponding to an anionic part were found to be present in a ratio of 1:1:1 through integration of the $^1$H NMR spectrum. When salicylanilide was used in an amount exceeding 2 equivalent weights, phosphonium, salicylanilide and 2,4-dihydroxy benzophenone were found to maintain the ratio of 1:1:1 through integration of the $^1$H NMR spectrum. Therefore, it was determined that the structure represented by Formula 2d was a stable form.

Preparative Example 20

Preparation of Phosphonium Compound Represented by Formula 2e 10.6 g of 2,6-diisopropylaniline and 8.3 g of salicylic acid were added to 300 g of chlorobenzene, followed by adding 4.1 g of PCl$_3$, which in turn was reacted under reflux for 3 hours. The resultant reaction solution was filtered while the solution was hot, which in turn was cooled to ambient temperature. The resultant reaction solution was recrystallized with ethanol/water, thereby affording a compound of formula 2e':

[Formula 2e']

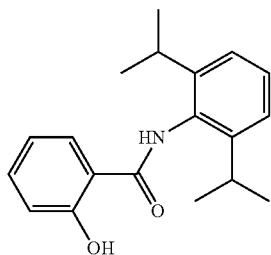

29.7 g of a compound of Formula 2e' was added to 100 g of MeOH, followed by adding 21.6 g of 25 wt % sodium methoxide solution, which in turn was completely dissolved while reacting at ambient temperature for 30 minutes. To the solution, 18.6 g of 2,2'-biphenol was added and dissolved, followed by slowly adding 43.5 g of the phosphenium bromide (salt) represented by Formula 1b' previously dissolved in 50 g of methanol. The mixture was allowed to further react for 1 hour. The resulting ivory solid was filtered to obtain 66.2 g of a compound. The compound was identified by NMR data as a compound represented by Formula 2e:

[Formula 2e]

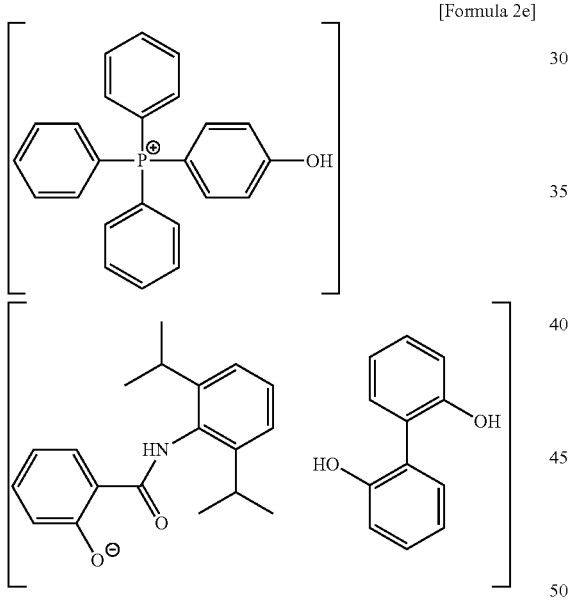

$^1$H NMR (300 MHz, DMSO) δ 10.90 (s, 2H), 8.08-7.82 (m, 4H), 7.82-7.58 (m, 11H), 7.33 (ddd, J=16.5, 10.4, 7.7 Hz, 4H), 7.24-7.14 (m, 4H), 7.12-6.96 (m, 4H), 6.92 (d, J=7.7 Hz, 1H), 6.85-6.68 (m, 5H), 3.07 (qd, J=13.6, 6.9 Hz, 2H), 1.13 (d, J=6.9 Hz, 12H).

In the compound represented by Formula 2e, phosphonium and the compound represented by Formula 2e' and 2,2'-biphenol corresponding to an anionic part were found to be present in a ratio of 1:1:1 through integration of the $^1$H NMR spectrum. When the compound represented by Formula 2e' was used in an amount exceeding 2 equivalent weights, phosphonium, the compound represented by Formula 2' and 2,2'-biphenol were found to maintain the ratio of 1:1:1 through integration of the $^1$H NMR spectrum. Therefore, it was determined that the structure represented by Formula 2e was a stable form.

Preparative Example 21

Preparation of Phosphonium Compound Represented by Formula 2f 26.3 g of 3-hydroxy 2-naphthanalide was added to 100 g of MeOH/DMF (weight ratio 1:1), followed by adding 21.6 g of 25 wt % sodium methoxide solution, which in turn was completely dissolved while reacting at ambient temperature for 30 minutes. To the solution, 21.4 g of 3,4-dihydroxy benzophenone was added and dissolved, followed by slowly adding 41.9 g of tetraphenylphosphonium bromide previously dissolved in 50 g of methanol. The mixture was allowed to further react for 1 hour. The resulting yellow solid was filtered to obtain 70.7 g of a compound. The compound was identified by NMR data as a compound represented by Formula 2f:

[Formula 2f]

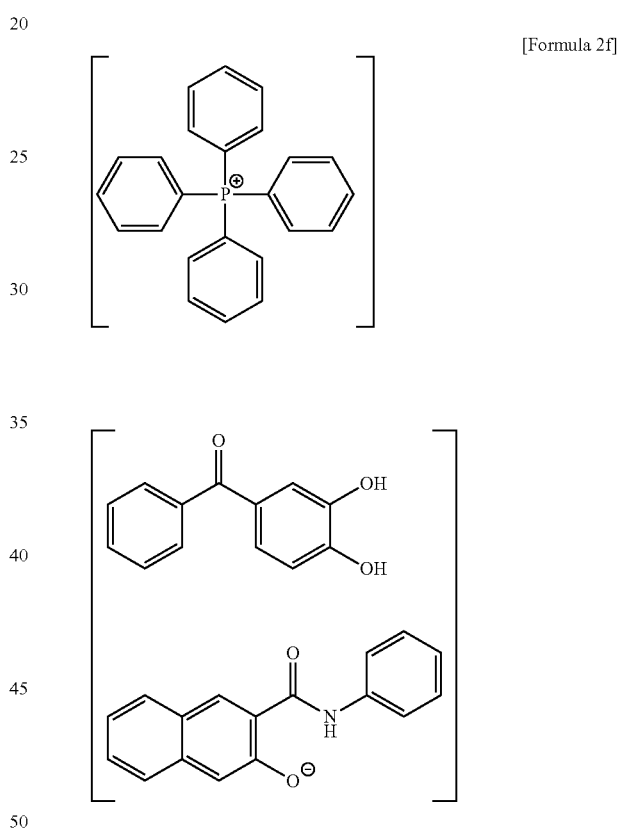

$^1$H NMR (300 MHz, DMSO) δ 8.36 (s, 1H), 7.97 (ddd, J=7.4, 5.5, 1.9 Hz, 4H), 7.77 (tdd, J=8.5, 7.3, 2.6 Hz, 17H), 7.67-7.46 (m, 6H), 7.42-7.27 (m, 3H), 7.25-7.15 (m, 2H), 7.08 (dd, J=8.3, 2.2 Hz, 1H), 7.01 (t, J=7.4 Hz, 1H), 6.93 (t, J=6.9 Hz, 1H), 6.82-6.72 (m, 2H).

In the compound represented by Formula 2f, phosphonium, 3-hydroxy 2-naphthanalide and 3,4-dihydroxybenzophenone corresponding to an anionic part were found to be present in a ratio of 1:1:1 through integration of the $^1$H NMR spectrum. When 3-hydroxy 2-naphthanalide was used in an amount exceeding 2 equivalent weights, phosphonium, 3-hydroxy 2-naphthanalide and 3,4-dihydroxybenzophenone were found to maintain the ratio of 1:1:1 through integration of the $^1$H NMR spectrum. Therefore, it was determined that the structure represented by Formula 2f was a stable form.

Preparative Example 22

Preparation of Phosphonium Compound Represented by Formula 2g 26.3 g of 3-hydroxy 2-naphthanalide was added to 100 g of MeOH, followed by adding 21.6 g of 25 wt % sodium methoxide solution, which in turn was completely dissolved while reacting at ambient temperature for 30 minutes. To the solution, 21.4 g of 3,4-dihydroxy benzophenone was added and dissolved, followed by slowly adding 41.9 g of tetraphenylphosphonium bromide previously dissolved in 50 g of methanol. The mixture was allowed to further react for 1 hour. The resulting ivory solid was filtered to obtain 66.9 g of a compound. The compound was identified by NMR data as a compound represented by Formula 2g:

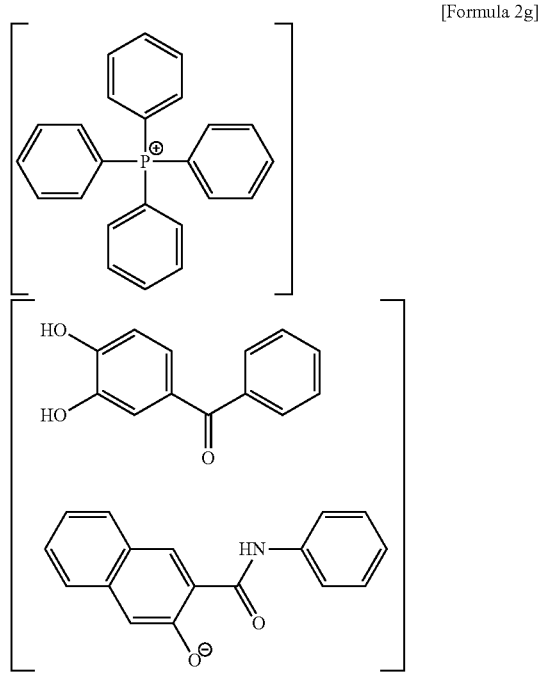

[Formula 2g]

$^1$H NMR (300 MHz, DMSO) δ 8.46 (s, 1H), 8.01-7.89 (m, 4H), 7.86-7.67 (m, 18H), 7.66-7.53 (m, 3H), 7.53-7.38 (m, 3H), 7.33 (t, J=7.9 Hz, 2H), 7.29-7.19 (m, 2H), 7.12-6.93 (m, 4H), 6.83 (d, J=8.3 Hz, 1H).

In the compound represented by Formula 2g, phosphonium, 3-hydroxy 2-naphthanalide and 3,4-dihydroxy benzophenone corresponding to an anionic part were found to be present in a ratio of 1:1:1 through integration of the $^1$H NMR spectrum. When 3-hydroxy 2-naphthanalide was used in an amount exceeding 2 equivalent weights, phosphonium, 3-hydroxy 2-naphthanalide, and 3,4-dihydroxybenzophenone were found to maintain the ratio of 1:1:1 through integration of the $^1$H NMR spectrum. Therefore, it was determined that the structure represented by Formula 2g was a stable form.

Preparative Example 23

Preparation of Phosphonium Compound Represented by Formula 2h 26.3 g of 3-hydroxy 2-naphthanalide was added to 100 g of MeOH/DMF (weight ratio 1:1), followed by adding 21.6 g of 25 wt % sodium methoxide solution, which in turn was completely dissolved while reacting at ambient temperature for 30 minutes. To the solution, 35.0 g of 4,4'-fluoren-9-ylidenebisphenol was added and dissolved, followed by slowly adding 43.5 g of the phosphenium bromide (salt) represented by Formula 1b' previously dissolved in 50 g of methanol. The mixture was allowed to further react for 1 hour. The resulting yellow solid was filtered to obtain 74.5 g of a compound. The compound was identified by NMR data as a compound represented by Formula 2h:

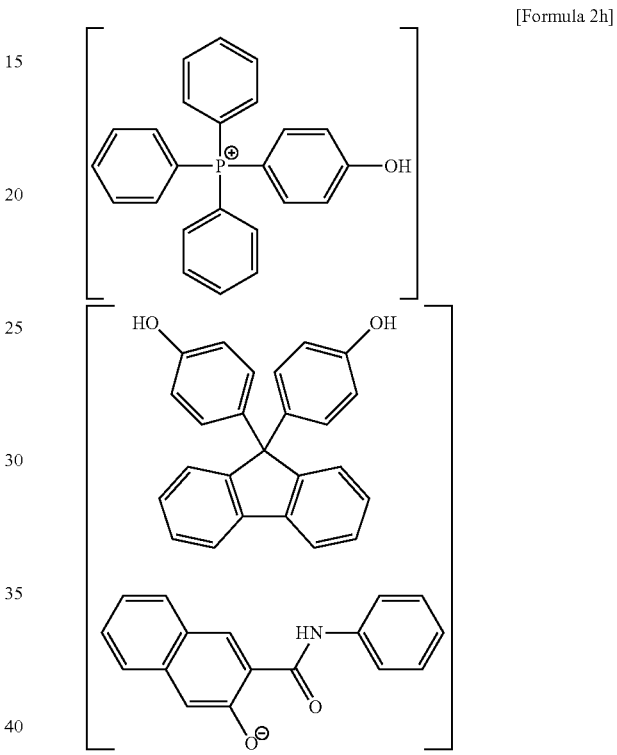

[Formula 2h]

$^1$H NMR (300 MHz, DMSO) δ 8.39 (s, 1H), 7.91 (ddd, J=14.3, 6.9, 2.6 Hz, 6H), 7.83-7.63 (m, 16H), 7.45 (d, J=8.6 Hz, 1H), 7.41-7.20 (m, 10H), 7.03 (dd, J=13.8, 7.1 Hz, 2H), 6.95-6.83 (m, 8H), 6.62 (d, J=8.7 Hz, 4H).

In the compound represented by Formula 2h, phosphonium, 3-hydroxy 2-naphthanalide and 4,4'-fluoren-9-ylidenebisphenol corresponding to an anionic part were found to be present in a ratio of 1:1:1 through integration of the $^1$H NMR spectrum. When 3-hydroxy 2-naphthanalide was used in an amount exceeding 2 equivalent weights, phosphonium, 3-hydroxy 2-naphthanalide and 4,4'-fluoren-9-ylidenebisphenol were found to maintain the ratio of 1:1:1 through integration of the $^1$H NMR spectrum. Therefore, it was determined that the structure represented by Formula 2h was a stable form.

Preparative Example 24

Preparation of Phosphonium Compound Represented by Formula 2i 21.3 g of salicylanilide was added to 100 g of MeOH/DMF (weight ratio 1:1), followed by adding 21.6 g of 25 wt % sodium methoxide solution, which in turn was completely dissolved while reacting at room temperature for 30 minutes. To the solution, 21.8 g of 4,4'-dihydroxydiphenyl sulfide was added and dissolved, followed by slowly adding 41.9 g of tetraphenylphosphonium bromide previously dissolved in 50 g of methanol. The mixture was allowed to further react for 1 hour. The resulting yellow solid was filtered to obtain 77.9 g of a compound. The compound was identified by NMR data as a compound represented by Formula 2i:

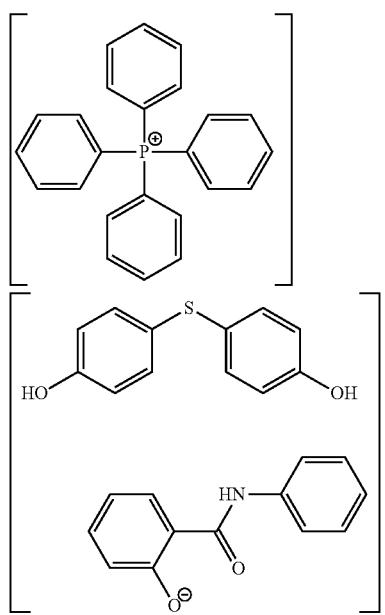

[Formula 2i]

$^1$H NMR (300 MHz, DMSO) δ 15.17 (s, 1H), 8.02-7.91 (m, 4H), 7.87-7.61 (m, 18H), 7.30-7.20 (m, 2H), 7.19-7.07 (m, 4H), 7.00-6.87 (m, 2H), 6.80-6.68 (m, 4H), 6.41 (dd, J=8.4, 1.0 Hz, 1H), 6.17 (ddd, J=7.9, 6.9, 1.2 Hz, 1H).

In the compound represented by Formula 2i, phosphonium and salicylanilide and 4,4'-dihydroxydiphenyl sulfide corresponding to an anionic part were found to be present in a ratio of 1:1:1 through integration of the $^1$H NMR spectrum. When salicylanilide was used in an amount exceeding 2 equivalent weights, phosphonium, salicylanilide and 4,4'-dihydroxydiphenyl sulfide were found to maintain the ratio of 1:1:1 through integration of the $^1$H NMR spectrum. Therefore, it was determined that the structure represented by Formula 2i was a stable form.

Preparative Example 25

Preparation of Phosphonium Compound Represented by Formula 2j 26.3 g of 3-hydroxy 2-naphthanalide was added to 100 g of MeOH/DMF (weight ratio 1:1), followed by adding 21.6 g of 25 wt % sodium methoxide solution, which in turn was completely dissolved while reacting at ambient temperature for 30 minutes. To the solution, 21.8 g of 4,4'-dihydroxydiphenyl sulfide was added and dissolved, followed by slowly adding 43.5 g of the phosphenium bromide (salt) represented by Formula 1b' previously dissolved in 50 g of methanol. The mixture was allowed to further react for 1 hour. The resulting yellow solid was filtered to obtain 76.6 g of a compound. The compound was identified by NMR data as a compound represented by Formula 2j:

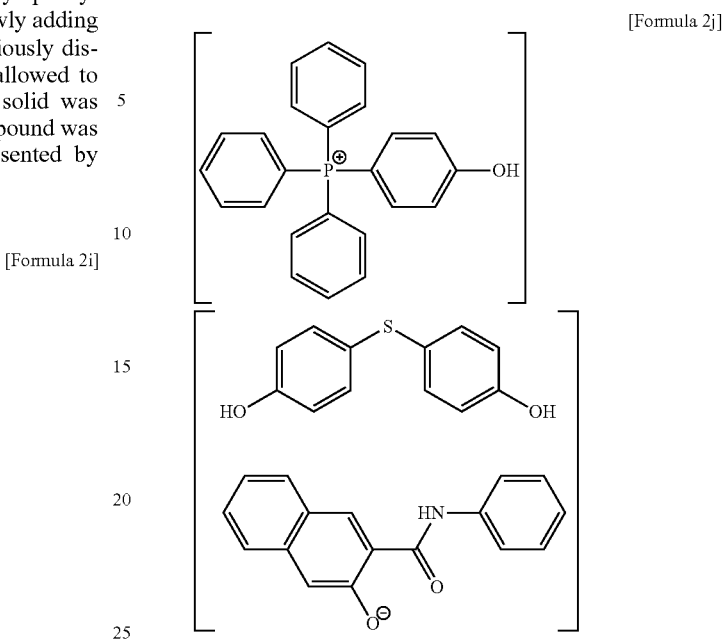

[Formula 2j]

$^1$H NMR (300 MHz, DMSO) δ 8.42 (s, 1H), 7.98-7.85 (m, 3H), 7.73 (dtd, J=12.5, 8.3, 2.5 Hz, 14H), 7.46 (d, J=8.4 Hz, 1H), 7.40-7.19 (m, 5H), 7.04 (t, J=7.4 Hz, 2H), 6.95 (dd, J=8.8, 3.0 Hz, 3H).

In the compound represented by Formula 2j, phosphonium, 3-hydroxy 2-naphthanalide and 4,4'-dihydroxydiphenyl sulfide corresponding to an anionic part were found to be present in a ratio of 1:1:1 through integration of the $^1$H NMR spectrum. When 3-hydroxy 2-naphthanalide was used in an amount exceeding 2 equivalent weights, phosphonium, 3-hydroxy 2-naphthanalide and 4,4'-dihydroxydiphenyl sulfide were found to maintain the ratio of 1:1:1 through integration of the $^1$H NMR spectrum. Therefore, it was determined that the structure represented by Formula 2j was a stable form.

Details of the components used in Examples and Comparative Examples are as follows.

(A) Epoxy Resin

NC-3000 (manufactured by Nippon Kayaku), a biphenyl type epoxy resin, was used.

(B) Curing Agent

HE100C-10 (manufactured by Air Water), a xyloc type phenol resin, was used.

(C) Curing Catalyst

Phosphonium compounds prepared in Preparative Examples 1 to 25 were used as (C1) to (C25).

(C26)

Triphenyl Phosphine (C27)

An adduct of triphenyl phosphine and 1,4-benzoquinone (D) Inorganic Filler

A mixture of spherical fused silica having an average particle diameter of 18 μm and spherical fused silica having an average particle diameter of 0.5 μm (in weight ratio of 9:1) was used.

(E) Coupling Agent

A mixture of (e1) mercaptopropyl trimethoxy silane, KBM-803 (manufactured by Shinetsu Co., Ltd.) and (e2) methyl trimethoxy silane, SZ-6070 (manufactured by Dow Corning Chemical Co., Ltd.) was used.

(F) Additives (f1) Carnauba wax as a release agent, and (f2) Carbon black, MA-600 (manufactured by Matsushita Chemical Co., Ltd.) as a coloring agent were used.

Examples and Comparative Examples

The components were weighed as listed in Table 1 to 3 (unit: parts by weight) and uniformly mixed using a Henschel mixer to prepare first powder compositions. Then, each of the compositions was melt-kneaded by a continuous kneader at 95° C., cooled, and pulverized to prepare an epoxy resin composition for encapsulation of a semiconductor device.

TABLE 1

| | | Example | | | | | | | | | | |
|---|---|---|---|---|---|---|---|---|---|---|---|---|
| | | 1 | 2 | 3 | 4 | 5 | 6 | 7 | 8 | 9 | 10 |
| (A) | | 8.6 | 8.6 | 8.6 | 8.6 | 8.6 | 8.6 | 8.6 | 8.6 | 8.6 | 8.6 |
| (B) | | 5.0 | 5.0 | 5.0 | 5.0 | 5.0 | 5.0 | 5.0 | 5.0 | 5.0 | 5.0 |
| (C) | C1 | 0.4 | — | — | — | — | — | — | — | — | — |
| | C2 | — | 0.4 | — | — | — | — | — | — | — | — |
| | C3 | — | — | 0.4 | — | — | — | — | — | — | — |
| | C4 | — | — | — | 0.4 | — | — | — | — | — | — |
| | C5 | — | — | — | — | 0.4 | — | — | — | — | — |
| | C6 | — | — | — | — | — | 0.4 | — | — | — | — |
| | C7 | — | — | — | — | — | — | 0.4 | — | — | — |
| | C8 | — | — | — | — | — | — | — | 0.4 | — | — |
| | C9 | — | — | — | — | — | — | — | — | 0.4 | — |
| | C10 | — | — | — | — | — | — | — | — | — | 0.4 |
| (D) | | 85 | 85 | 85 | 85 | 85 | 85 | 85 | 85 | 85 | 85 |
| (E) | (e1) | 0.2 | 0.2 | 0.2 | 0.2 | 0.2 | 0.2 | 0.2 | 0.2 | 0.2 | 0.2 |
| | (e2) | 0.2 | 0.2 | 0.2 | 0.2 | 0.2 | 0.2 | 0.2 | 0.2 | 0.2 | 0.2 |
| (F) | (f1) | 0.3 | 0.3 | 0.3 | 0.3 | 0.3 | 0.3 | 0.3 | 0.3 | 0.3 | 0.3 |
| | (f2) | 0.3 | 0.3 | 0.3 | 0.3 | 0.3 | 0.3 | 0.3 | 0.3 | 0.3 | 0.3 |

TABLE 2

| | | Example | | | | | | | | | |
|---|---|---|---|---|---|---|---|---|---|---|---|
| | | 11 | 12 | 13 | 14 | 15 | 16 | 17 | 18 | 19 | 20 |
| (A) | | 8.6 | 8.6 | 8.6 | 8.6 | 8.6 | 8.6 | 8.6 | 8.6 | 8.6 | 8.6 |
| (B) | | 5.0 | 5.0 | 5.0 | 5.0 | 5.0 | 5.0 | 5.0 | 5.0 | 5.0 | 5.0 |
| (C) | C11 | 0.4 | — | — | — | — | — | — | — | — | — |
| | C12 | — | 0.4 | — | — | — | — | — | — | — | — |
| | C13 | — | — | 0.4 | — | — | — | — | — | — | — |
| | C14 | — | — | — | 0.4 | — | — | — | — | — | — |
| | C15 | — | — | — | — | 0.4 | — | — | — | — | — |
| | C16 | — | — | — | — | — | 0.4 | — | — | — | — |
| | C17 | — | — | — | — | — | — | 0.4 | — | — | — |
| | C18 | — | — | — | — | — | — | — | 0.4 | — | — |
| | C19 | — | — | — | — | — | — | — | — | 0.4 | — |
| | C20 | — | — | — | — | — | — | — | — | — | 0.4 |
| (D) | | 85 | 85 | 85 | 85 | 85 | 85 | 85 | 85 | 85 | 85 |
| (E) | (e1) | 0.2 | 0.2 | 0.2 | 0.2 | 0.2 | 0.2 | 0.2 | 0.2 | 0.2 | 0.2 |
| | (e2) | 0.2 | 0.2 | 0.2 | 0.2 | 0.2 | 0.2 | 0.2 | 0.2 | 0.2 | 0.2 |
| (F) | (f1) | 0.3 | 0.3 | 0.3 | 0.3 | 0.3 | 0.3 | 0.3 | 0.3 | 0.3 | 0.3 |
| | (f2) | 0.3 | 0.3 | 0.3 | 0.3 | 0.3 | 0.3 | 0.3 | 0.3 | 0.3 | 0.3 |

TABLE 3

| | | Example | | | | | Comparative example | |
|---|---|---|---|---|---|---|---|---|
| | | 21 | 22 | 23 | 24 | 25 | 1 | 2 |
| (A) | | 8.6 | 8.6 | 8.6 | 8.6 | 8.6 | 8.6 | 8.6 |
| (B) | | 5.0 | 5.0 | 5.0 | 5.0 | 5.0 | 5.0 | 5.0 |
| (C) | C21 | 0.4 | — | — | — | — | — | — |
| | C22 | — | 0.4 | — | — | — | — | — |
| | C23 | — | — | 0.4 | — | — | — | — |
| | C24 | — | — | — | 0.4 | — | — | — |
| | C25 | — | — | — | — | 0.4 | — | — |
| | C26 | — | — | — | — | — | 0.4 | — |
| | C27 | — | — | — | — | — | — | 0.4 |
| (D) | | 85 | 85 | 85 | 85 | 85 | 85 | 85 |
| (E) | (e1) | 0.2 | 0.2 | 0.2 | 0.2 | 0.2 | 0.2 | 0.2 |
| | (e2) | 0.2 | 0.2 | 0.2 | 0.2 | 0.2 | 0.2 | 0.2 |
| (F) | (f1) | 0.3 | 0.3 | 0.3 | 0.3 | 0.3 | 0.3 | 0.3 |
| | (f2) | 0.3 | 0.3 | 0.3 | 0.3 | 0.3 | 0.3 | 0.3 |

The epoxy resin compositions prepared in Examples and Comparative Examples were evaluated for their physical properties by way of the following measuring methods. Results are summarized in Tables 4 to 6.

(1) Flowability (inches): The flow length of each of the epoxy resin compositions was measured using a transfer molding press in a testing mold (Fujuwa sek, TEP12-16EV) at 175° C. and 70 kgf/cm² in accordance with EMMI-1-66. A higher measured value indicates better flowability.

(2) Curing shrinkage (%): Each of the epoxy resin compositions was molded using a transfer molding press in an ASTM mold for flexural strength specimen construction at 175° C. and 70 kgf/cm² to obtain a molded specimen (125×12.6×6.4 mm). The specimen was subjected to post-molding cure (PMC) in an oven at 170° C.-180° C. for 4 hours. After cooling to 25° C., the length of the specimen was measured using calipers. Curing shrinkage of the epoxy resin composition was calculated by Equation 1:

Curing shrinkage=|C−D|/C×100 wherein C is the length of a specimen obtained by transfer molding of an epoxy resin composition at 175° C. under a load of 70 kgf/cm², and D is the length of the specimen after post-curing the specimen at 170° C. to 180° C. for 4 hours and cooling.

(3) Glass transition temperature (° C.) was measured using a thermomechanical analyzer (TMA) while heating at a rate of 10° C./min from 25° C. to 300° C.

(4) Moisture absorption (%): Each of the resin compositions prepared in the Examples and Comparative Examples was molded at a mold temperature of 170° C. to 180° C., a clamp pressure of 70 kg/cm², a transfer pressure of 1,000 psi and a transfer speed of 0.5-1 cm/s for a curing time of 120 sec to obtain a cured specimen in the form of a disc having a diameter of 50 mm and a thickness of 1.0 mm. The specimen was subjected to post-molding curing (PMC) in an oven at 170° C. to 180° C. for 4 hours and allowed to stand at 85° C. and 85 RH % for 168 hours. The weights of the specimen before and after moisture absorption were measured. The moisture absorption of the resin composition was calculated by Equation 2:

Moisture absorption (%)=(Weight of the specimen after moisture absorption−Weight of the specimen before moisture absorption)÷(Weight of the specimen before moisture absorption)×100

(5) Adhesive strength (kgf): A copper metal device having a size adapted to a mold for adhesive strength measurement was prepared as a test piece. Each of the resin compositions prepared in the Examples and Comparative Examples was molded on the test piece at a mold temperature of 170° C. to 180° C., a clamp pressure of 70 kgf/cm², a transfer pressure of 1,000 psi and a transfer speed of 0.5-1 cm/s for a curing time of 120 sec to obtain a cured specimen. The specimen was subjected to post-molding cure (PMC) in an oven at 170° C. to 180° C. for 4 hours. The area of the epoxy resin composition in contact with the specimen was 40±1 mm². The adhesive strength of the epoxy resin composition was measured using a universal testing machine (UTM). 12 specimens of each composition were produced. After the measurement procedure was repeated, the measured adhesive strength values were averaged.

(6) Degree of cure (Shore-D): Each of the epoxy resin compositions was cured using a multi plunger system (MPS) equipped with a mold at 175° C. for 50 sec, 60 sec, 70 sec, 80 sec, and 90 sec to construct exposed thin quad flat packages (eTQFPs), each including a copper metal device having a width of 24 mm, a length of 24 mm and a thickness of 1 mm. The hardness values of the cured products in the packages on the mold according to the curing periods of time were directly measured using a Shore D durometer. A higher hardness value indicates better degree of cure.

(7) Storage stability (%): The flow length of each of the epoxy resin compositions was measured in accordance with the method described in (1) while storing the compositions for one week in a thermo-hygrostat set to at 25° C./50% RH at an interval of 24 hours. Percent (%) of the flow length after storage to the flow length immediately after the preparation of the composition was calculated. A higher value indicates better storage stability.

TABLE 4

| | | | Example | | | | | | | | | |
|---|---|---|---|---|---|---|---|---|---|---|---|---|
| | | | 1 | 2 | 3 | 4 | 5 | 6 | 7 | 8 | 9 | 10 |
| Basic physical properties | Flowability (inch) | | 76 | 77 | 72 | 74 | 70 | 77 | 76 | 63 | 68 | 71 |
| | Curing shrinkage (%) | | 0.35 | 0.37 | 0.34 | 0.35 | 038 | 0.36 | 0.36 | 0.35 | 0.34 | 0.40 |
| | Glass transition temp. (° C.) | | 122 | 123 | 124 | 125 | 124 | 125 | 128 | 122 | 126 | 122 |
| | Moisture absorption (%) | | 0.24 | 0.24 | 0.24 | 0.24 | 0.23 | 0.24 | 0.21 | 0.24 | 0.20 | 0.25 |
| | Adhesive strength (kgf) | | 75 | 75 | 74 | 72 | 74 | 75 | 73 | 77 | 74 | 73 |
| Evaluation of packages | Degree of cure (Shore-D) according to curing time | 40 sec | 67 | 67 | 65 | 64 | 66 | 67 | 69 | 67 | 66 | 72 |
| | | 50 sec | 70 | 74 | 71 | 69 | 72 | 71 | 72 | 72 | 72 | 74 |
| | | 60 sec | 74 | 76 | 73 | 74 | 75 | 73 | 74 | 74 | 75 | 76 |
| | | 70 sec | 75 | 76 | 75 | 75 | 76 | 76 | 77 | 75 | 76 | 77 |
| | | 80 Sec | 75 | 78 | 76 | 75 | 76 | 78 | 78 | 75 | 76 | 78 |
| | Storage stability | 24 hr | 94% | 96% | 95% | 96% | 95% | 97% | 98% | 94% | 96% | 96% |
| | | 48 hr | 90% | 93% | 93% | 93% | 94% | 95% | 95% | 90% | 91% | 93% |
| | | 72 hr | 85% | 93% | 89% | 90% | 90% | 92% | 91% | 85% | 87% | 90% |

TABLE 5

| | | Example | | | | | | | | | |
|---|---|---|---|---|---|---|---|---|---|---|---|
| | | 11 | 12 | 13 | 14 | 15 | 16 | 17 | 18 | 19 | 20 |
| Basic physical properties | Flowability (inch) | 77 | 68 | 73 | 69 | 75 | 68 | 69 | 69 | 67 | 71 |
| | Curing shrinkage (%) | 0.33 | 0.34 | 0.37 | 0.38 | 0.34 | 0.40 | 0.33 | 0.38 | 0.35 | 0.36 |
| | Glass transition temp (° C.) | 124 | 124 | 121 | 124 | 127 | 126 | 124 | 124 | 127 | 126 |
| | Moisture absorption (%) | 0.22 | 0.30 | 0.24 | 0.24 | 0.23 | 0.25 | 0.22 | 0.24 | 0.23 | 023 |
| | Adhesive strength (kgf) | 75 | 72 | 75 | 74 | 75 | 73 | 75 | 74 | 75 | 75 |
| Evaluation of packages | Degree of cure (Shore-D) according to curing time | 40 sec | | | | | | | | | |
| | | 74 | 75 | 72 | 74 | 69 | 69 | 70 | 70 | 69 | 61 |
| | | 50 sec | | | | | | | | | |
| | | 75 | 77 | 74 | 76 | 74 | 73 | 75 | 76 | 74 | 69 |
| | | 60 sec | | | | | | | | | |
| | | 76 | 77 | 76 | 76 | 75 | 76 | 76 | 76 | 75 | 76 |
| | | 70 sec | | | | | | | | | |
| | | 76 | 77 | 76 | 76 | 77 | 77 | 76 | 76 | 77 | 76 |
| | | 50 Sec | | | | | | | | | |
| | | 78 | 78 | 78 | 77 | 78 | 78 | 78 | 77 | 78 | 77 |
| | Storage stability | 24 hr | 97% | 95% | 97% | 94% | 96% | 96% | 97% | 94% | 96% | 97% |
| | | 48 hr | 95% | 91% | 96% | 90% | 93% | 93% | 94% | 90% | 92% | 95% |
| | | 72 hr | 94% | 87% | 93% | 85% | 88% | 89% | 94% | 88% | 89% | 88% |

TABLE 6

| | | Example | | | | | Comparative Example | |
|---|---|---|---|---|---|---|---|---|
| | | 21 | 22 | 23 | 24 | 25 | 1 | 2 |
| Basic physical properties | Flowability (inch) | 69 | 66 | 67 | 64 | 70 | 51 | 61 |
| | Curing shrinkage (%) | 0.36 | 0.37 | 0.35 | 0.38 | 0.37 | 0.41 | 0.42 |
| | Glass transition temp. (° C.) | 126 | 125 | 127 | 125 | 124 | 126 | 124 |
| | Moisture absorption (%) | 0.24 | 0.25 | 0.26 | 0.25 | 0.24 | 0.26 | 0.26 |
| | Adhesive strength (kgf) | 75 | 74 | 73 | 73 | 75 | 74 | 76 |
| Evaluation of packages | Degree of cure (Shore-D) according to curing time | 40 sec | | | | | | |
| | | 66 | 65 | 65 | 67 | 64 | 51 | 66 |
| | | 50 sec | | | | | | |
| | | 70 | 69 | 71 | 70 | 72 | 56 | 68 |
| | | 60 sec | | | | | | |
| | | 72 | 73 | 72 | 74 | 73 | 58 | 69 |
| | | 70 sec | | | | | | |
| | | 75 | 76 | 74 | 74 | 75 | 62 | 72 |
| | | 80 Sec | | | | | | |
| | | 76 | 76 | 76 | 75 | 75 | 63 | 74 |
| | Storage stability | 24 hr | 93% | 93% | 94% | 95% | 92% | 85% | 89% |
| | | 48 hr | 89% | 90% | 89% | 91% | 87% | 72% | 79% |
| | | 72 hr | 86% | 88% | 85% | 86% | 84% | 58% | 68% |

It may be seen that the epoxy resin compositions prepared in Examples 1 to 25 exhibited higher flowability and higher degrees of curing even in shorter curing periods of time in view of curability for each curing period of time than the compositions of Comparative Examples 1 and 2. For storage stability, it may be seen that the epoxy resin compositions of the Examples exhibited less change in flowability after 72 hours.

On the contrary, the compositions prepared in Comparative Examples (not including the phosphonium compound) exhibited low storage stability, high curing shrinkage, and low flowability. Therefore, it may be be seen that the composition of Comparative Examples in a package could not ensure the desired effects.

By way of summation and review, in transfer molding, modification of epoxy resins or phenol resins as curing agents may lead to improvements in the characteristics and reliability of semiconductor devices.

Such epoxy resin compositions may include an epoxy resin, a curing agent, a curing catalyst, and the like. As the curing catalyst, imidazole catalysts, amine catalysts, and phosphine catalysts may be utilized.

With the trend toward compact, lightweight and high-performance electronic devices, high integration of semiconductor devices has been accelerated year by year. Some issues may arise with increasing demand for surface mounting of semiconductor devices. Packaging materials for semiconductor devices may exhibit rapid curability to improve productivity and storage stability to improve handling performance during distribution and storage.

An epoxy resin curing catalyst may use tri-substituted phosphoniophenolates or salts thereof.

The embodiments may provide a compound for curing catalysts capable of accelerating curing of an epoxy resin, having good flowability upon molding and high curing strength, and being curable even at short curing periods of time.

The embodiments may provide a compound for curing catalysts capable of accelerating curing of an epoxy resin at a low temperature.

The embodiments may provide a compound for curing catalysts having high storage stability which catalyzes curing only at a desired curing temperature but does not show any curing activity at temperatures deviating from desired curing temperatures.

The embodiments may provide a compound for curing catalysts having high storage stability, which is capable of accelerating curing of an epoxy resin and curing of an epoxy resin at low temperature while minimizing viscosity change in a mixture including the compound, an epoxy resin, a curing agent and the like even within desired ranges of time and temperature, thereby ensuring that the epoxy resin composition obtained after curing at high temperature does not exhibit any deterioration in moldability, mechanical, electrical, and chemical properties of molded products due to decrease in flowability.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A phosphonium compound represented by one of the following Formulae 1a to 1o:

[Formula 1a]

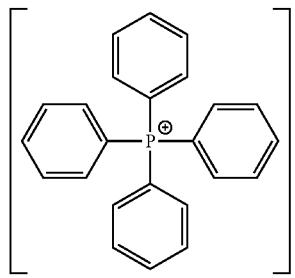

[Formula 1b]

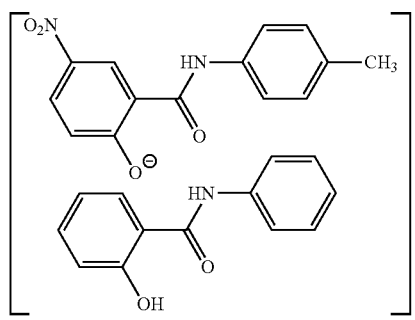

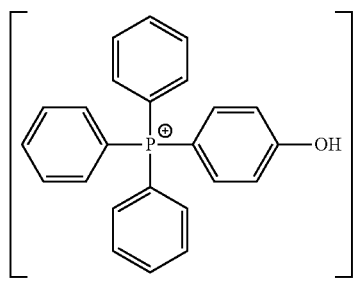

[Formula 1c]

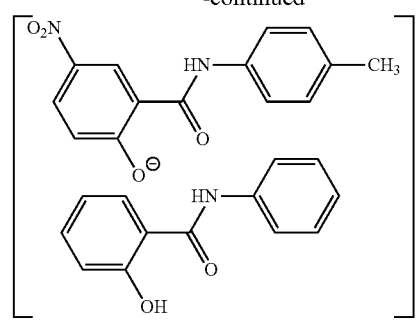

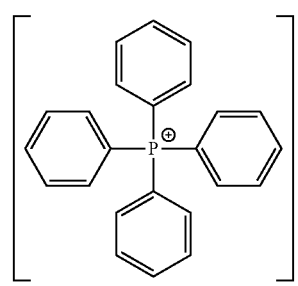

[Formula 1d]

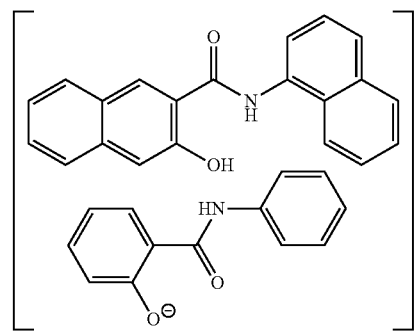

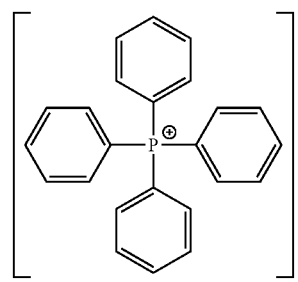

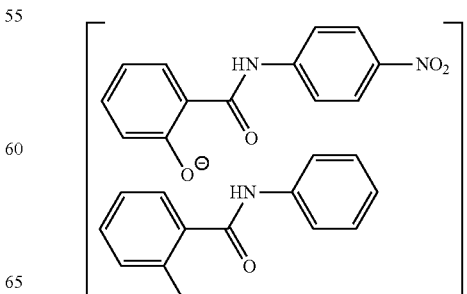

[Formula 1e]
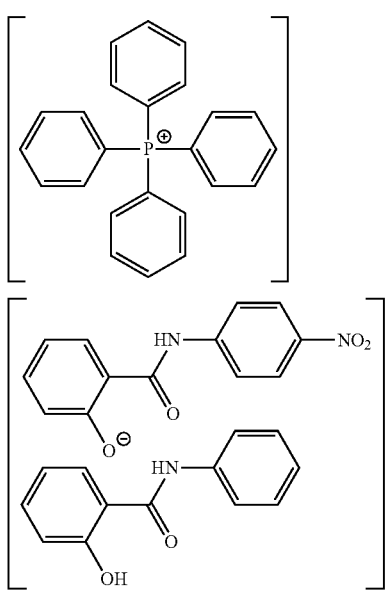
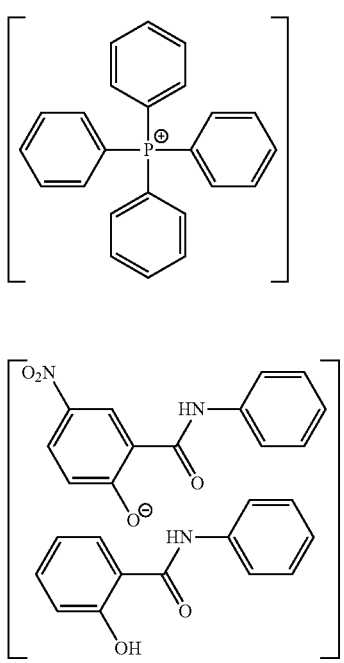
[Formula 1f]
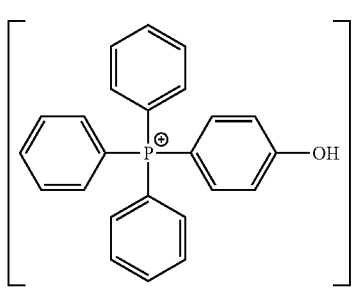
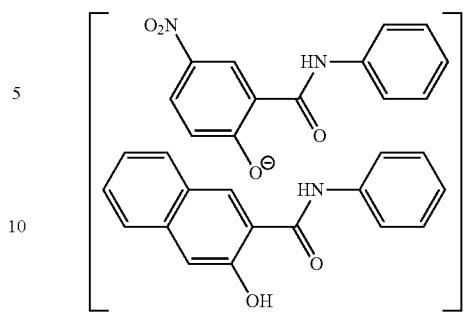
[Formula 1h]
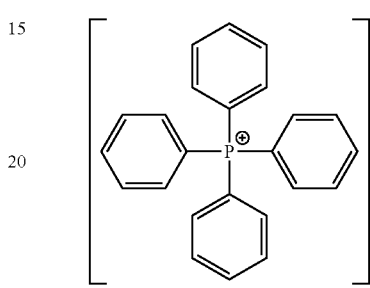
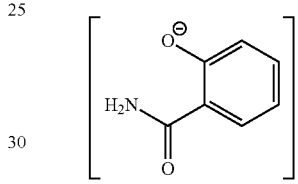
[Formula 1i]
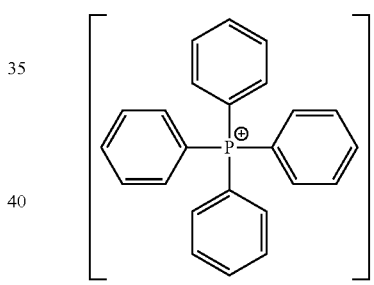
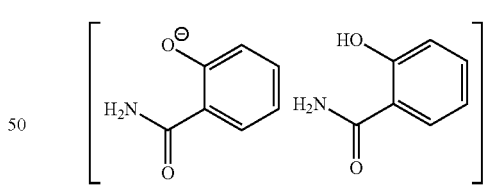
[Formula 1g]
[Formula 1j]
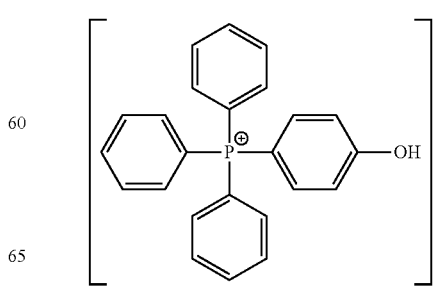

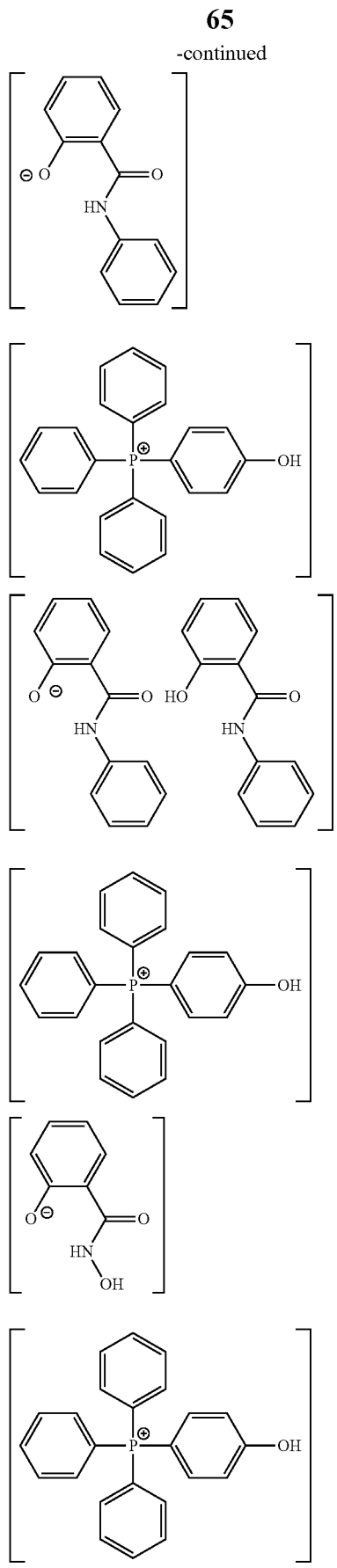

[Formula 1k]

[Formula 1l]

[Formula 1m]

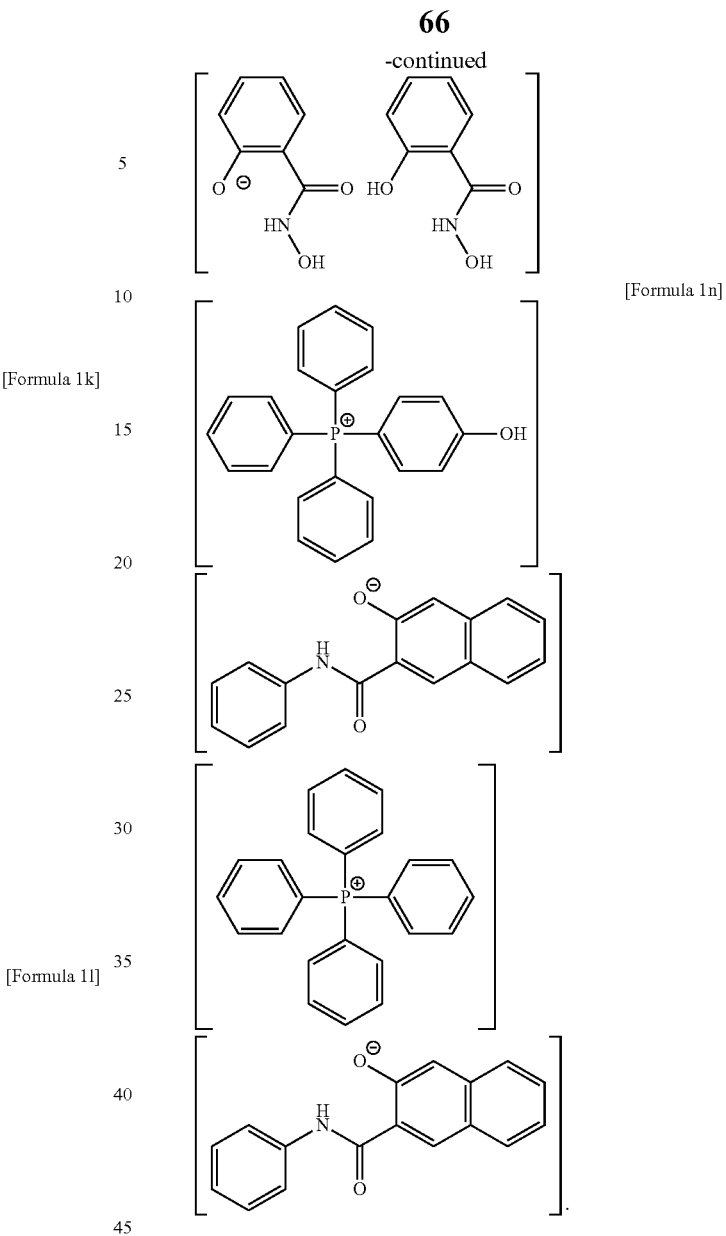

[Formula 1n]

2. A method of preparing the phosphonium compound as claimed in claim 1, the method comprising reacting a phosphonium cation-containing compound with an anilide anion-containing compound.

3. An epoxy resin composition, comprising:
an epoxy resin,
a curing agent,
inorganic filler, and
a curing catalyst, wherein the curing catalyst includes the phosphonium compound as claimed in claim 1.

4. The epoxy resin composition as claimed in claim 3, wherein the epoxy resin includes at least one of bisphenol A epoxy resin, bisphenol F epoxy resin, phenol novolac epoxy resin, tert-butyl catechol epoxy resin, naphthalene epoxy resin, glycidyl amine epoxy resin, cresol novolac epoxy resin, biphenyl epoxy resin, linear aliphatic epoxy resin, cycloaliphatic epoxy resin, heterocyclic epoxy resin, spiro ring-containing epoxy resin, cyclohexane dimethanol epoxy resin, trimethylol epoxy resin, and halogenated epoxy resin.

5. The epoxy resin composition as claimed in claim 3, wherein the curing agent includes a phenol resin.

6. The epoxy resin composition as claimed in claim 3, wherein the curing agent includes at least one of phenolaralkyl phenol resin, phenol novolac phenol resin, xyloc phenol resin, cresol novolac phenol resin, naphthol phenol resin, terpene phenol resin, multifunctional phenol resin, dicyclopentadiene-based phenol resin, novolac phenol resin synthesized from bisphenol A and resol, a polyhydric phenol compound, an acid anhydride, and an aromatic amine.

7. The epoxy resin composition as claimed in claim 3, wherein the curing catalyst is present in the composition in an amount of 0.01 wt % to 5 wt %, based on a total weight of the epoxy resin composition.

8. The epoxy resin composition as claimed in claim 3, wherein the phosphonium compound is present in the curing catalyst in an amount of 10 wt % to 100 wt %, based on a total weight of the curing catalyst.

9. The epoxy resin composition as claimed in claim 3, wherein the epoxy resin composition has a storage stability of 80% or more, as calculated by the Equation 2:

Storage stability=$(F1-F0)/F0 \times 100$, wherein F1 is a flow length in inches of the epoxy resin composition measured after storing the composition at 25° C./50% RH for 72 hours using a transfer molding press at 175° C. and 70 kgf/cm² in accordance with EMMI-1-66, and F0 is an initial flow length in inches of the epoxy resin composition.

10. The epoxy resin composition as claimed in claim 3, wherein the epoxy resin composition has a curing shrinkage rate of less than 0.4%, as calculated by the Equation 1:

Curing shrinkage=$|C-D|/C \times 100$, wherein C is a length of a specimen obtained by subjecting an epoxy resin composition to a transfer molding at 175° C. under a load of 70kgf/cm², and D is a length of the specimen after post-curing the specimen at 170° C. to 180° C. for 4 hours and cooling.

11. A semiconductor device encapsulated with the epoxy resin composition as claimed in claim 3.

12. The epoxy resin composition as claimed in claim 3, further comprising a silicone oil modified with a functional group.

13. The epoxy resin composition as claimed in claim 12, wherein the modified silicone oil is at least one selected from the group of silicone oil having an epoxy functional group, silicone oil having an amine functional group, silicone oil having a carboxyl functional group, and a combination thereof.

14. The epoxy resin composition as claimed in claim 12, wherein the modified silicone oil is included in the composition in an amount of 0.05 wt % to 1.5 wt %, based on a total weight of the epoxy resin composition.

15. A phosphonium compound represented by one of the following Formulae 2a to 2j:

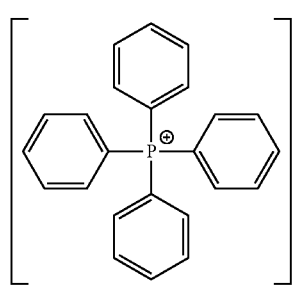

[Formula 2a]

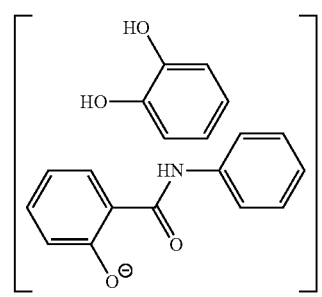

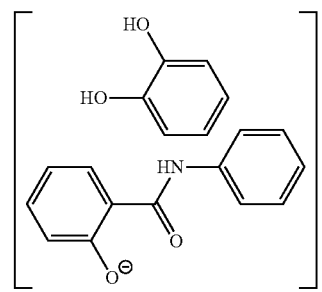

[Formula 2b]

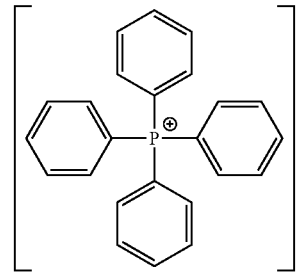

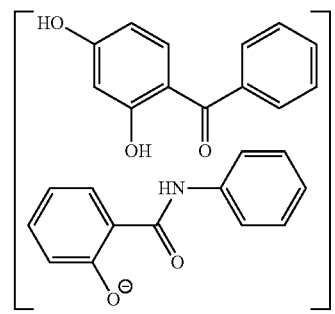

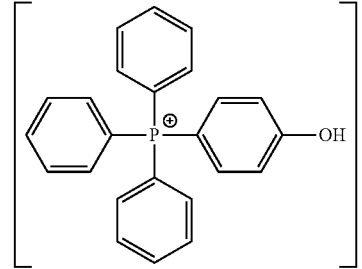

[Formula 2c]

[Formula 2d]
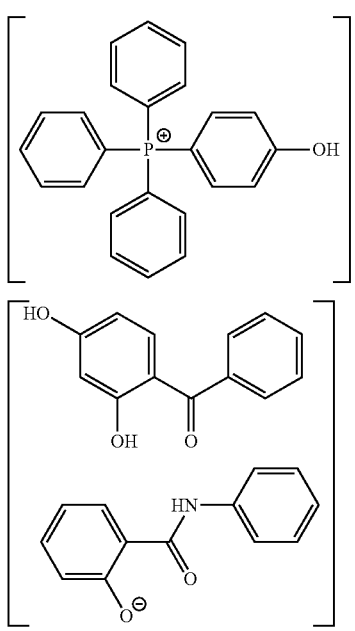
[Formula 2e]
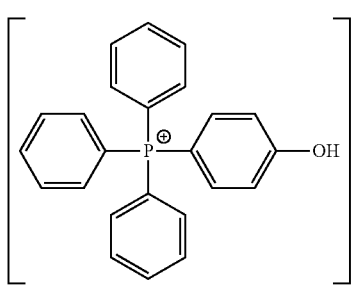
[Formula 2f]
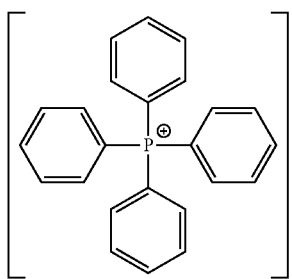
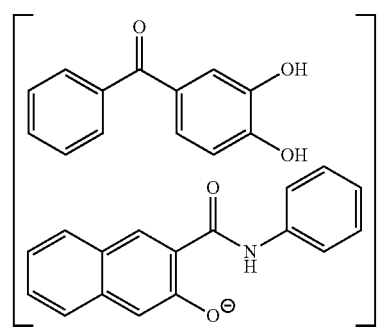
[Formula 2g]
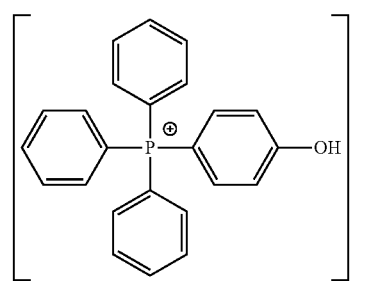
[Formula 2h]
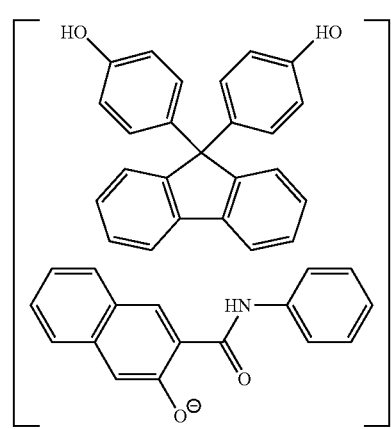

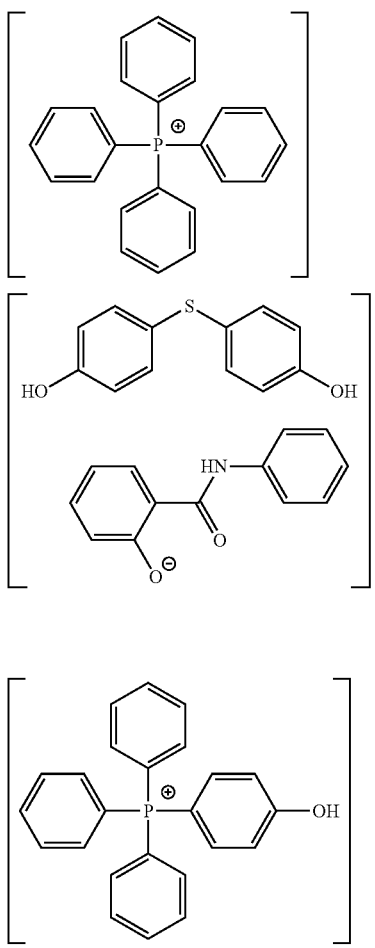

[Formula 2i]

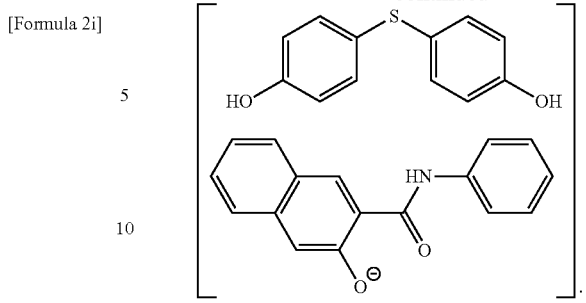

16. A method of preparing the phosphonium compound as claimed in claim 15, the method comprising reacting a phosphonium cation-containing compound with an anilide anion-containing compound.

17. An epoxy resin composition, comprising:
   an epoxy resin,
   a curing agent,
   inorganic filler, and
   a curing catalyst, wherein the curing catalyst includes the phosphonium compound as claimed in claim 15.

18. A semiconductor device encapsulated with the epoxy resin composition as claimed in claim 17.

19. The epoxy resin composition as claimed in claim 17, further comprising a silicone oil modified with a functional group.

[Formula 2j]

20. The epoxy resin composition as claimed in claim 19, wherein the modified silicone oil is at least one selected from the group of silicone oil having an epoxy functional group, silicone oil having an amine functional group, silicone oil having a carboxyl functional group, and a combination thereof.

21. The epoxy resin composition as claimed in claim 19, wherein the modified silicone oil is included in the composition in an amount of 0.05 wt % to 1.5 wt %, based on a total weight of the epoxy resin composition.

\* \* \* \* \*